United States Patent
Gerber et al.

(10) Patent No.: US 9,750,862 B2
(45) Date of Patent: Sep. 5, 2017

(54) ADAPTIVE SYSTEM FOR BLOOD FLUID REMOVAL

(75) Inventors: Martin Gerber, Maple Grove, MN (US); John Burnes, Coon Rapids, MN (US); Suping Lyu, Maple Grove, MN (US); VenKatesh R. Manda, Stillwater, MN (US); Bryant Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/424,533

(22) Filed: Mar. 20, 2012

(65) Prior Publication Data
US 2012/0277722 A1    Nov. 1, 2012

Related U.S. Application Data

(60) Provisional application No. 61/480,539, filed on Apr. 29, 2011, provisional application No. 61/480,544, (Continued)

(51) Int. Cl.
*A61M 1/16*  (2006.01)
*A61B 5/145*  (2006.01)
(Continued)

(52) U.S. Cl.
CPC ......... *A61M 1/1603* (2014.02); *A61B 5/0031* (2013.01); *A61B 5/026* (2013.01); *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01);
(Continued)

(58) Field of Classification Search
CPC ...... A61M 1/14; A61M 1/1603; G06Q 50/22; G06Q 50/24
USPC ............................................ 705/2–3; 604/29
See application file for complete search history.

(56) References Cited

U.S. PATENT DOCUMENTS 3,608,729 A    9/1971    Haselden
3,669,878 A    6/1972    Marantz
(Continued)

FOREIGN PATENT DOCUMENTS

CN          103037917          4/2013
EP          266795 A2          11/1987
(Continued)

OTHER PUBLICATIONS

PCT/US2012/034331 International Search Report, Jul. 9, 2012.
(Continued)

*Primary Examiner* — Luke Gilligan
(74) *Attorney, Agent, or Firm* — Kenneth Collier; Roger Hahn

(57) ABSTRACT

Methods for monitoring patient parameters and blood fluid removal system parameters include identifying those system parameters that result in improved patient parameters or in worsened patient parameters. By comparing the patient's past responses to system parameters or changes in system parameters, a blood fluid removal system may be able to avoid future use of parameters that may harm the patient and may be able to learn which parameters are likely to be most effective in treating the patient in a blood fluid removal session.

9 Claims, 12 Drawing Sheets

Related U.S. Application Data filed on Apr. 29, 2011, provisional application No. 61/480,541, filed on Apr. 29, 2011, provisional application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.

| | | |
|---|---|---|
| *A61B 5/00* | (2006.01) | |
| *A61B 5/026* | (2006.01) | |
| *A61B 5/053* | (2006.01) | |
| *A61M 1/34* | (2006.01) | |
| *B01D 65/02* | (2006.01) | |
| *A61M 1/00* | (2006.01) | |
| *A61B 5/0295* | (2006.01) | |
| *A61M 1/14* | (2006.01) | |
| *B01D 61/00* | (2006.01) | |
| *B01D 61/32* | (2006.01) | |
| *A61M 1/36* | (2006.01) | |
| *A61M 1/28* | (2006.01) | |

(52) U.S. Cl.
CPC ........ *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/28* (2013.01); *A61M 1/34* (2013.01); *A61M 1/342* (2013.01); *A61M 1/3607* (2014.02); *A61M 1/3609* (2014.02); *A61M 1/3672* (2013.01); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/005* (2013.01); *A61M 2230/20* (2013.01); *A61M 2230/207* (2013.01); *A61M 2230/208* (2013.01); *A61M 2230/65* (2013.01); *B01D 2321/12* (2013.01); *B01D 2321/40* (2013.01)

(56) References Cited

U.S. PATENT DOCUMENTS

| | | |
|---|---|---|
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Nason |
| 4,685,903 A | 8/1987 | Cable |
| 4,750,494 A | 6/1988 | King |
| 4,826,663 A | 5/1989 | Alberti |
| 4,828,693 A | 5/1989 | Lindsay |
| 5,080,653 A | 1/1992 | Voss |
| 5,092,886 A | 3/1992 | Dobos-Hardy |
| 5,097,122 A | 3/1992 | Colman |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,507,723 A * | 4/1996 | Keshaviah ............ A61M 1/16 210/647 |
| 5,683,432 A | 11/1997 | Goedeke |
| 5,762,782 A | 6/1998 | Kenley |
| 5,902,336 A | 5/1999 | Mishkin |
| 5,944,684 A | 8/1999 | Roberts |
| 6,048,732 A | 4/2000 | Anslyn |
| 6,052,622 A | 4/2000 | Holmstrom |
| 6,058,331 A | 5/2000 | King |
| 6,156,002 A | 12/2000 | Polaschegg |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,505,075 B1 | 1/2003 | Weiner |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,676,608 B1 | 1/2004 | Keren |
| 6,689,083 B1 | 2/2004 | Gelfand |
| 6,706,007 B2 | 3/2004 | Gelfand |
| 6,711,439 B1 | 3/2004 | Bradley |
| 6,726,647 B1 | 4/2004 | Sternby |
| 6,780,322 B1 | 8/2004 | Bissler |
| 6,818,196 B2 | 11/2004 | Wong |
| 6,878,283 B2 | 4/2005 | Thompson |
| 6,887,214 B1 | 5/2005 | Levin |
| 6,890,315 B1 | 5/2005 | Levin |
| 6,960,179 B2 | 11/2005 | Gura |
| 7,074,332 B2 | 7/2006 | Summerton |
| 7,077,819 B1 | 7/2006 | Goldau |
| 7,175,809 B2 | 2/2007 | Gelfand |
| 7,208,092 B2 | 4/2007 | Micheli |
| 7,276,042 B2 | 10/2007 | Polaschegg |
| 7,399,289 B2 | 7/2008 | Gelfand |
| 7,500,958 B2 | 3/2009 | Asbrink |
| 7,566,432 B2 | 7/2009 | Wong |
| 7,575,564 B2 | 8/2009 | Childers |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,775,983 B2 | 8/2010 | Zhang |
| 7,776,210 B2 | 8/2010 | Rosenbaum |
| 7,785,463 B2 | 8/2010 | Bissler |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,000,000 B2 | 8/2011 | Greenberg |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |

(56) References Cited

U.S. PATENT DOCUMENTS

| | | |
|---|---|---|
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,282,828 B2 | 10/2012 | Wallenas |
| 8,292,594 B2 | 10/2012 | Tracey |
| 8,313,642 B2 | 11/2012 | Yu et al. |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding |
| 8,409,441 B2 | 4/2013 | Wilt |
| 8,496,809 B2 | 7/2013 | Roger |
| 8,499,780 B2 | 8/2013 | Wilt |
| 8,500,676 B2 | 8/2013 | Jansson |
| 8,512,271 B2 | 8/2013 | Moissl |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 2002/0042561 A1 | 4/2002 | Schulman et al. |
| 2002/0112609 A1 | 8/2002 | Wong |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0068219 A1 | 4/2004 | Summerton |
| 2004/0099593 A1 | 5/2004 | DePaolis |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1* | 6/2005 | Bissler et al. .................. 210/87 |
| 2005/0126998 A1 | 6/2005 | Childers |
| 2005/0131331 A1 | 6/2005 | Kelly |
| 2005/0150832 A1 | 7/2005 | Tsukamoto |
| 2005/0234381 A1 | 10/2005 | Niemetz |
| 2005/0236330 A1 | 10/2005 | Nier |
| 2005/0274658 A1 | 12/2005 | Rosenbaum |
| 2006/0025661 A1 | 2/2006 | Sweeney et al. |
| 2006/0058731 A1 | 3/2006 | Burnett |
| 2006/0195064 A1 | 8/2006 | Plahey |
| 2006/0217771 A1 | 9/2006 | Soykan |
| 2006/0226079 A1 | 10/2006 | Mori et al. |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross et al. |
| 2008/0093276 A1 | 4/2008 | Roger |
| 2008/0215247 A1 | 9/2008 | Tonelli et al. |
| 2008/0253427 A1 | 10/2008 | Kamen |
| 2009/0020471 A1 | 1/2009 | Tsukamoto |
| 2009/0101577 A1 | 4/2009 | Fulkerson et al. |
| 2009/0124963 A1 | 5/2009 | Hogard |
| 2009/0127193 A1 | 5/2009 | Updyke |
| 2009/0171261 A1 | 7/2009 | Sternby |
| 2009/0264776 A1 | 10/2009 | Vardy |
| 2009/0275849 A1 | 11/2009 | Stewart |
| 2009/0275883 A1* | 11/2009 | Chapman et al. .............. 604/29 |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0010429 A1* | 1/2010 | Childers et al. ................ 604/29 |
| 2010/0042035 A1 | 2/2010 | Moissl |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem et al. |
| 2010/0113891 A1 | 5/2010 | Barrett |
| 2010/0114012 A1 | 5/2010 | Sandford |
| 2010/0137693 A1 | 6/2010 | Porras |
| 2010/0137782 A1 | 6/2010 | Jansson |
| 2010/0168546 A1 | 7/2010 | Kamath |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2011/0017665 A1 | 1/2011 | Updyke |
| 2011/0048949 A1 | 3/2011 | Ding |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0144570 A1 | 6/2011 | Childers |
| 2011/0184340 A1 | 7/2011 | Tan |
| 2011/0272337 A1 | 11/2011 | Palmer |
| 2011/0301447 A1 | 12/2011 | Park |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0259276 A1 | 10/2012 | Childers |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217029 A1 | 8/2014 | Meyer |
| 2014/0217030 A1 | 8/2014 | Meyer |

(56) References Cited

U.S. PATENT DOCUMENTS

| | | |
|---|---|---|
| 2014/0220699 A1 | 8/2014 | Pudil |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0250427 A1 | 9/2015 | Soykan |
| 2015/0352269 A1 | 12/2015 | Gerber |
| 2015/0367054 A1 | 12/2015 | Gerber |
| 2016/0206801 A1 | 7/2016 | Gerber |
| 2016/0331884 A1 | 11/2016 | Sigg |

FOREIGN PATENT DOCUMENTS

| | | | |
|---|---|---|---|
| EP | 1124599 | | 5/2000 |
| EP | 1175238 | | 11/2000 |
| EP | 2308526 | | 10/2003 |
| EP | 1364666 | A1 | 11/2003 |
| EP | 1523347 | | 1/2004 |
| EP | 1523350 | | 1/2004 |
| EP | 0906768 | B1 | 2/2004 |
| EP | 1691863 | | 4/2005 |
| EP | 2116269 | | 2/2008 |
| EP | 1450879 | | 10/2008 |
| EP | 1514562 | | 4/2009 |
| EP | 2219703 | | 5/2009 |
| EP | 1592494 | B1 | 6/2009 |
| EP | 2100553 | A1 | 9/2009 |
| EP | 2398529 | | 11/2010 |
| EP | 2575827 | A2 | 12/2010 |
| EP | 2100553 | | 8/2011 |
| EP | 2576453 | A2 | 12/2011 |
| EP | 2701580 | | 11/2012 |
| EP | 2701595 | | 11/2012 |
| EP | 1345856 | B1 | 3/2013 |
| EP | 2344220 | B1 | 4/2013 |
| EP | 1351756 | | 7/2013 |
| EP | 2190498 | | 7/2013 |
| EP | 2701596 | | 3/2014 |
| EP | 1582226 | | 1/2016 |
| JP | 2002542900 | | 12/2002 |
| JP | 2003235965 | | 8/2003 |
| JP | 5099464 | | 10/2012 |
| WO | 9503839 | | 2/1995 |
| WO | WO 9532010 A1 * | | 11/1995 ............ A61M 1/16 |
| WO | 9937342 | | 7/1999 |
| WO | 0057935 | | 10/2000 |
| WO | 0066197 | | 11/2000 |
| WO | 0066197 | A1 | 11/2000 |
| WO | 0185295 | A2 | 11/2001 |
| WO | 0185295 | A2 | 11/2001 |
| WO | 03043677 | A2 | 5/2003 |
| WO | 03043680 | | 5/2003 |
| WO | 03051422 | A2 | 6/2003 |
| WO | 2004008826 | | 1/2004 |
| WO | 2004009156 | | 1/2004 |
| WO | 2004009158 | | 1/2004 |
| WO | 0170307 | A1 | 4/2004 |
| WO | 2004030716 | A2 | 4/2004 |
| WO | 2004030717 | A2 | 4/2004 |
| WO | 2004064616 | A2 | 8/2004 |
| WO | 2005061026 | | 7/2005 |
| WO | 2005123230 | A2 | 12/2005 |
| WO | 2006011009 | | 2/2006 |
| WO | 2006017446 | | 2/2006 |
| WO | 2007038347 | | 4/2007 |
| WO | 2007089855 | A2 | 8/2007 |
| WO | 2008037410 | | 4/2008 |
| WO | 2009026603 | | 12/2008 |
| WO | 2009024566 | | 2/2009 |
| WO | 2009026603 | A1 | 3/2009 |
| WO | 2009061608 | | 5/2009 |
| WO | 2009094184 | | 7/2009 |
| WO | 2009157877 | A1 | 12/2009 |
| WO | 2009157878 | A1 | 12/2009 |
| WO | 2010028860 | A1 | 2/2010 |
| WO | 0128860 | A1 | 3/2010 |
| WO | 2010024963 | | 3/2010 |
| WO | 2010033699 | | 3/2010 |
| WO | 2010077851 | | 7/2010 |
| WO | 2010096659 | | 10/2010 |
| WO | 2010121820 | | 10/2010 |
| WO | 2011025705 | A1 | 3/2011 |
| WO | 2011026645 | | 3/2011 |
| WO | 2011137693 | | 11/2011 |
| WO | 2012042323 | | 4/2012 |
| WO | 2012050781 | | 4/2012 |
| WO | 2012051996 | | 4/2012 |
| WO | 20122073420 | | 6/2012 |
| WO | 2012148781 | | 11/2012 |
| WO | 2012148786 | | 11/2012 |
| WO | 2012148787 | A1 | 11/2012 |
| WO | 2012148789 | | 11/2012 |
| WO | 2012162515 | A2 | 11/2012 |
| WO | 2012172398 | | 12/2012 |
| WO | 2013019179 | A1 | 2/2013 |
| WO | 2013019994 | A2 | 2/2013 |
| WO | 2013025844 | | 2/2013 |
| WO | 2013028809 | A3 | 2/2013 |
| WO | 2013101292 | | 7/2013 |
| WO | 2013103607 | A1 | 7/2013 |
| WO | 2013103906 | | 7/2013 |
| WO | 2013110906 | | 8/2013 |
| WO | 2013110919 | | 8/2013 |
| WO | 2013114063 | A1 | 8/2013 |
| WO | 2013121162 | A1 | 8/2013 |
| WO | 2013140346 | | 9/2013 |
| WO | 2013141896 | | 9/2013 |
| WO | 2013101292 | A3 | 10/2013 |
| WO | 14066254 | | 5/2014 |
| WO | 14066255 | | 5/2014 |
| WO | 14077082 | | 5/2014 |
| WO | 2014121162 | | 8/2014 |
| WO | 2014121163 | | 8/2014 |
| WO | 2014121167 | | 8/2014 |
| WO | 2014121169 | | 8/2014 |

OTHER PUBLICATIONS

U.S. Appl. No. 61/480,539.
U.S. Appl. No. 61/480,541.
U.S. Appl. No. 61/480,535.
U.S. Appl. No. 61/480,532.
U.S. Appl. No. 61/480,530.
U.S. Appl. No. 61/480,528.
Roberts M, The regenerative dialysis (REDY) sorbent system, Nephrology, 1998, 275-278 : 4.
Brynda, et. al., The detection of human β2-microglobulin by grating coupler immunosensor with three dimensional antibody networks, Biosensors & Bioelectronics, 1999, 363-368, 14(4).
Nedelkov, et. al., Design of buffer exchange surfaces and sensor chips for biosensor chip mass spectrometry, Proteomics, 2002, 441-445, 2(4).
Hemametrics, Crit-Line Hematocrit Accuracy, 2003, 1-5, vol. 1, Tech Note No. 11 (Rev. D).
Siegenthalar, et. al., Pulmonary fluid status monitoring with intrathoracic impedance, Journal of Clinical Monitoring and Computing, 2010, 449-451 : 24.
Wang, Fundamentals of intrathoracic impedance monitoring in heart failure, Am. J. Cardiology, 2007, 3G-310 : Suppl.
Bleyer, et. al., Sudden and cardiac death rates in hemodialysis patients, Kidney International, 1999, 1553-1559 : 55.
Zhong, et. al., Miniature urea sensor based on H(+)-ion sensitive field effect transistor and its application in clinical analysis, Chin. J. Biotechnol., 1992, 57-65, 8(1).
PCT/US2012/034331 International Search Report. Jul. 9, 2012.
PCT/US2012/034334 International Search Report, Jul. 6, 2012.
PCT/US2012/034335 International Search Report, Sep. 5, 2012.
PCT/US/2013/034327 International Search Report, Aug. 13, 2013.
PCT/US/2012/034329 International Search Report, Dec. 3, 2012.

(56) References Cited

OTHER PUBLICATIONS

Wheaton, et al., Dowex Ion Exchange Resins-Fundamentals of Ion Exchange; Jun. 2000, pp. 1-9. http://www.dow.com/scripts/litorder.asp? filepath=liquidseps/pdfs/noreg/177-01837.pdf.
Lima, et. al., An electrochemical sensor based on nanostructure hollsndite-type manganese oxide for detection of potassium ion, Sensors, 2009, 6613-8625, 9.
MacLean, ET, AL., Effects of hindlimb contraction on pressor and muscle interstitial metabolite responses in the cat, J. App. Physiol., 1998, 1583-1592, 85 (4).
Overgaard, et. al., Activity-induced recovery of excitability in K+-depressed rat soieus muscle, Am. J. P.
Overgaard. et. al., Relations between excitability and contractility in rate soleus'muscle: role of the NA+-K+ pump and NA+-K-S gradients. Journal of Physiology, 1999, 215-225, 518(1).
PCT/US2012/034332, International Search Report, dated Jul. 5, 2012.
U.S. Non Provisional Application, U.S. Appl. No. 13/368,225.
Redfield, et. al, Restoration of renal response to atria! natriuretic factor in experimental low-output heat failure, Am. J. Physiol., 1989, R917-923:257.
Rogoza, et. al., Validation of A&D UA-767 device for the self-measurement of blood pressure, Blood Pressure Monitoring, 2000, 227-231, 5(4).
Ronco et al. 2008, 'Cardiorenal Syndrome,' Journal American College Cardiology, 52:1527-1539, Abstract.
Secemsky, et. al, High prevalence of cardiac autonomic dysfunction and T-wave alternans in dialysis patients. Heart Rhythm, Apr. 2011, 592-598 : vol. 8, No. 4.
U.S. Appl. No. 13/424,533.
U.S. Appl. No. 13/424,467.
U.S. Appl. No. 13/424,429.
U.S. Appl. No. 13/424,454.
U.S. Appl. No. 13/424,479.
U.S. Appl. No. 13/424,490.
U.S. Appl. No. 13/424,517.
U.S. Appl. No. 13/424,525.
U.S. Appl. No. 61/480,544.
Wei, et. al., Fullerene-cryptand coated piezoelectric crystal urea sensor based on urease, Analytica Chimica Acta, 2001, 77-85:437.
PCT/US2014/067650 International Search Report Written Opinion dated Mar. 9, 2015.
PCT/US2012/034335, International Preliminary Report on Patentability, dated Nov. 7, 2013.
Gambro AK 96 Dialysis Machine Operator's Manual, Dec. 2012.
Office Action in U.S. Appl. No. 13/757,792 dated Apr. 6, 2015.
PCT/US2012/034329, International Preliminary Report on Patentability, dated Oct. 29, 2013.
U.S. Appl. No. 13/757,794, filed Feb. 2, 2013.
U.S. Appl. No. 13/757,722, filed Feb. 1, 2013.
U.S. Appl. No. 13/837,287, filed Mar. 15, 2013.
U.S. Appl. No. 13/757,792, filed Feb. 2, 2013.
U.S. Appl. No. 13/791,755, filed Mar. 8, 2013.
PCT/US2014/014357 International Search Report and Written Opinion.
Leifer et al., 'A Study on the Temperature Variation of Rise Velocity for Large Clean Bubbles,' J. Atmospheric & Oceanic Tech., vol. 17, pp. 1392-1402.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, 'Terminal Velocity of a Bubble Rise in a Liquid Column,' World Acad. of Sci., Engineering & Tech., vol. 28, pp. 264-68.
The FHN Trial Group. In-Center. Hemodialysis Six Times per Week versus Three Times per Week, New England Journal of Medicine, 2010 Abstract.
U.S. Appl. No. 13/757,693, filed Feb. 1, 2013.
Coast, et al. 1990, An approach to Cardiac Arrhythmia analysis Using Hidden Markov Models, IEEE Transactions on Biomedical Engineering. 1990, 37 (9):826-835.
PCT/US2012/034330, International Preliminary Report on Patentability, dated Oct. 29, 2013.
PCT Application, PCT/US20013/020404, filed Jan. 4, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, dated Oct. 29, 2013.
PCT/US2012/034333, International Search Report, dated Aug. 29, 2013.
U.S. Appl. No. 13/757,794, filed Feb. 2, 2012.
Bleyer, et. al., Sudden and cardiac death rated in hemodialysis patients, Kidney International. 1999, 1553-1559: 55.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, Pa.
U.S. Appl. No. 13/424,517 IDS, filed Aug. 2, 2012.
U.S. Appl. No. 13/424,517, IDS filed Dec. 2, 2013.
PCT/US2012/034332, Internatonal Preliminary Report on Patentability, dated Oct. 29, 2013.
PCT/US2012/034303, Internationa Search Report, dated Jul. 6, 2013.
PCT/US2012/034327, International Preliminary Report on Patentability, dated Oct. 29, 2013.
Zoccali, Pulmonary Congestion Predicts Cardiac Events and Mortality in ESRD, Clinical Epidemiology, J. Am Soc Nephrol 24:639-646, 2013.
Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.
Whitman, CKD and Sudden Cardiac Death: Epidemiology, Mechanisms, and Therapeutic Approaches, J Am Soc Nephrol, 23:1929-1939, 2012.
Hall, Hospitalization for Congestive Heart Failure: United States, 2000-2010, NCHS Data Brief, No. 108, Oct. 2012.
Albert, Fluid Management Strategies in Heart Failure, Critical Care Nurse, 32:20-32, 2012.
PCT/US2014/065201 International Search Report dated May 26, 2015.
John Wm Agar: "Review: Understnading sorbent dialysis systems," Nephrology, vol. 15, No. 4, Jun. 1, 2010, pp. 406-411.

* cited by examiner

ADAPTIVE SYSTEM FOR BLOOD FLUID REMOVAL

FIELD

This application claims priority to U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each priority application was filed Apr. 29, 2011, wherein each priority application is hereby incorporated by reference in its entirety to the extent that it does not conflict with the disclosure presented herein.

FIELD

The present disclosure relates generally to devices, systems and methods for monitoring patient and system parameters of blood fluid removal sessions.

BACKGROUND

Patients who undergo hemodialysis or other procedures that remove fluid from blood often die of cardiac complications. Many factors may contribute to such death, including stress placed on the heart due to the increased blood fluid volume in these patients. Increased fluid concentrations and inability to appropriately remove waste products from the blood can also contribute to electrolyte and pH imbalance that can affect cardiac contractility and efficiency. Further, rapid changes in fluid volume or pH or electrolyte concentration of the blood during hemodialysis or other fluid removal processes may place additional stress on the heart and may contribute to the high rate of morbidity for patients who undergo blood fluid removal procedures.

When a patient reaches a point where routine blood fluid removal procedures are prescribed, the patient undergoes periodic examinations that allow a healthcare provider to set various parameters of the blood fluid removal procedures, such as the profile of fluid removal, the composition of dialysate or replacement fluid employed, and the like. These examinations typically occur once a month in accordance with current standards of care.

While such monthly examinations somewhat provide for blood fluid removal sessions tailored according to the patient's needs, it may be desirable to provide a more systematic evaluation of the patient and the blood fluid removal session parameters to achieve a more patient-specific therapy.

SUMMARY

This disclosure, among other things, describes devices, systems and methods for monitoring patient parameters and blood fluid removal system parameters and identifying those system parameters that result in improved (more effective) patient parameters or in worsened (less effective) patent parameters. By comparing the patient's past responses to system parameters or changes in system parameters, a blood fluid removal system may be able to avoid future use of parameters that may harm the patient and may be able to learn which parameters are likely to be most effective in treating the patient in a blood fluid removal session.

In various embodiments described herein, a method includes (i) initiating a blood fluid removal session with initial system parameters; (ii) acquiring a first set of data regarding one or more patient physiological parameters; (iii) storing the first data set in a "best" or "most effective to date" data set memory; (iv) associating the initial system parameters in an increased effectiveness lookup table with the first data set; (v) adjusting at least one parameter of the blood fluid removal session to arrive at adjusted system parameters; (vi) acquiring a second set of data regarding the one or more patient physiological parameters after the at least one parameter of the blood fluid removal session has been adjusted; and (vii) if at least one value of the second data set is closer to the target value than a corresponding value of at least one value of the first data set: replacing the first data set in the most effective to date data set memory with the second data set; storing in the increased effectiveness lookup table data regarding the second data set; and associating data regarding the adjusted system parameters with the second data set.

In embodiments, a method carried out by a blood fluid removal system includes (i) acquiring data regarding one or more of one or more patient physiological parameters and time since last blood fluid removal session; (ii) acquiring data regarding one or more target outcomes of a blood fluid removal session; (iii) determining whether at least one of the one or more target outcomes is within a predetermined range of a at least one corresponding prior target outcome stored in a lookup table, wherein the lookup table comprises data regarding system parameters used in one or more prior blood fluid removal sessions of the patient; (iv) determining whether the at least one target outcome was achieved with the system parameters used in the prior blood fluid removal session; (v) if the at least one target outcome is determined to have been achieved, determining whether at least one of the patient parameters or time since last blood fluid removal session is within a predetermined range of at least one corresponding parameter stored in the lookup table; and (vi) initiating a blood fluid removal session employing the system parameters used for the prior blood fluid removal session if the at least one patient parameter or time since last blood fluid removal session is determined to be within a predetermined range.

In embodiments, a method carried out by a blood fluid removal system includes (i) collecting first data regarding a patient, the data including one or more of a physiological parameter and time since last blood fluid removal session; (ii) collecting second data regarding system parameters employed in blood fluid removal sessions of the patient; (iii) determining, based on the first and second collected data, whether at least one physiological parameter of the patient improved as a result of the system parameters employed; (iv) determining whether a value of current patient data is within a predetermined range of a corresponding value of first collected data; and (v) employing the system parameters that resulted in improvement, if such parameters are determined to exist and if the current patient data is determined to be within the predetermined range.

Blood fluid removal systems configured to carry out the methods described herein are also presented, as are computer readable medium that, when executed, cause a blood fluid removal system to carry out the methods described herein.

One or more embodiments of the systems, devices and methods described herein may provide one or more advantages over prior systems, devices and methods for blood fluid removal in patients. Such advantages will be apparent to those skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
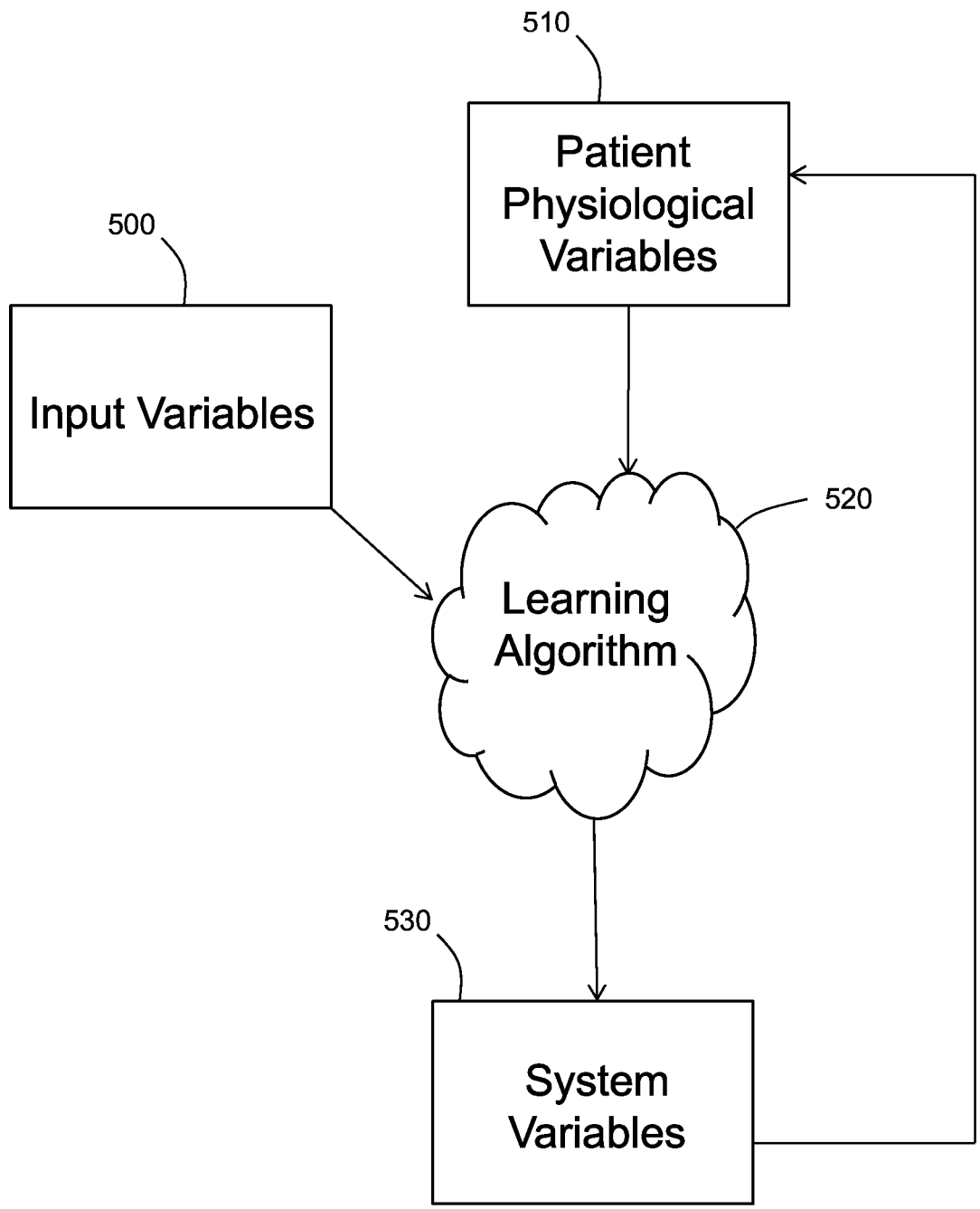
FIGS. 1-7 are flow diagrams illustrating methods in accordance with various embodiments described herein.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute kidney failure. Often such patients are stage 3 to stage 5 chronic kidney disease patients, are unresponsive or under-responsive to diuretics, or the like.

As used herein, a "blood fluid removal process," or the like, refers to a process from which fluid is removed from blood of a patient and the blood is returned to the patient. In most cases, the blood is also cleaned; i.e., waste products are removed from the blood and cleaned blood is returned to the patient. Examples of blood fluid removal processes include ultrafiltration, hemofiltration, hemodialysis, hemodiafiltration, peritoneal dialysis and the like. Any patient for which blood fluid removal is indicated may benefit from the devices, systems and methods described herein.

As used herein, "effective" or the like, as it relates to patient parameters, refers to the how close one or more patient parameters are to one or more target for the one or more parameters. Thus, a "most effective" patient parameter to date is a patient parameter at a given time that is closer to the target than the same parameter measured at any previous time. A "more effective" patient parameter is a parameter measured at a given time that is closer to the target than the same parameter measured at another time. A "least effective" patient parameter to date is a patient parameter at a given time that is farther from the target than the same parameter measured at any previous time. A "less effective" patient parameter is a parameter measured or observed at a given time that is farther from the target than the same parameter measured at another time.

This disclosure, among other things, describes devices, systems and methods for monitoring patient physiological parameters and blood fluid removal system parameters and identifying those system parameters that result in improved or more effective physiological parameters or in worsened physiological parameters. By comparing the patient's past responses to system parameters or changes in system parameters, a blood fluid removal system may be able to avoid future use of parameters that may harm the patient and may be able to learn which parameters are likely to be most effective in treating the patient in a blood fluid removal session.

Referring to FIG. 1, a high level schematic overview of embodiments of the present disclosure is shown. As shown in FIG. 1, a learning algorithm 520 is employed to determine what system parameters work well to produce desired patient physiological results based on input. Any suitable input variable 500 may be considered by the algorithm 520 in the learning process. For example, variables such as how long it has been since the patient's last blood removal session may be input. Such input could be important as patients undergoing, for example, hemodialysis on a Monday, Wednesday, Friday schedule are most likely to suffer an adverse cardiac event just prior to, during or after the Monday blood fluid removal session. Accordingly, the algorithm 520 may consider whether a different set of system parameters should be employed when the patient has not undergone a session in 72 hours relative to when the patient has not undergone a session in 48 hours. Input variables 500 may also include whether the patient has limited time to undergo a blood fluid removal session. The algorithm 520 can determine whether a faster fluid removal rate should be used or whether a partial session at a reduced fluid removal rate would likely be most effective based on the patient's history of response to fast fluid removal rates. Alternatively, the patient may have additional time to undergo a blood fluid removal session, and the algorithm 520 can take such input 500 into account to determine whether there may be an advantage to slower fluid removal rates or slower adjustment of a concentration of an electrolyte based on the patient's history. Of course, it will be understood that any other suitable input variables 500 may be entered regarding target outcomes (e.g., quick session, long session, etc.), patient history (e.g., time since last session), or the like. In embodiments, input that takes into account future patient behavior or needs may be entered into the system. For example, if a patient knows that they will miss a session or the time until their next session will be delayed from normal, time until next session may be entered, which may affect the system parameters (e.g., may remove additional fluid, etc.). By way of another example, if the patient knows that they will eat or drink an amount more than optimal before the session, expected consumption levels may be input in the system.

As shown in FIG. 1, the algorithm 520, based on input variables 500, and patient physiological variables 510 may determine appropriate system variables 530 to employ based on the patient's history with blood fluid sessions under the algorithm. During a blood fluid session, system variables 530 may be changed and the patient physiological response may be monitored in response to the changed system variables. If one or more of the patient's physiological variables 510 improve or become "more effective", the algorithm 530 can associate the changed system variables 530 with the increased effectiveness patient outcome so that the changed system variables 530 may be used later in the session or in a future session when the patient has a similar set of physiological variables 510. If one or more of the patient's physiological variables 510 become less effective, the algorithm 530 can associate the changed system variables 530 with a less effective patient outcome so that the changed system variables 530 may be avoided later in the session or in a future session when the patient has a similar set of physiological variables 510.

In embodiments, the physiological variables 510 are monitored by sensors that feed data regarding the variables directly into the algorithm 520 or electronics running the algorithm. The sensors may monitor fluid volume in the patient's blood; fluid volume in the patient's tissue; concentrations of electrolytes in the patient's blood; pH of the patient's blood; one or more cardiovascular parameter of the patient, such as blood pressure, heart rhythm, heart rate; or combinations or indicators thereof. The sensors may monitor the patient physiological parameters before, during or after a blood fluid removal session.

Any suitable sensor may be employed. Examples of sensors and systems that may be employed with regard to blood fluid volumes and tissue fluid volumes are discussed in U.S. Provisional Patent Application No. 61/480,528, filed on Apr. 29, 2011, entitled FLUID VOLUME MONITORING FOR PATIENTS WITH RENAL DISEASE; and U.S. Provisional Patent Application No. 61/480,530, filed on Apr. 29, 2011, entitled MONITORING FLUID VOLUME FOR PATIENTS WITH RENAL DISEASE, which applications are hereby incorporated herein by reference in their respective entireties to the extent that they do not conflict with the present disclosure. Sensors for monitoring tissue fluid volume, blood fluid volume, fluid flow or volume diverted from blood and the like typically monitor fluid indirectly, and directly monitor an indicator of fluid volume, flow or the like. For example, a sensor may indirectly monitor hematocrit (the portion of the blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used and may serve as an indicator of blood fluid volume. A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well-studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

Examples of sensors and systems for monitoring pH and electrolyte concentration are disclosed in U.S. Provisional Patent Application No. 61/480,532, filed on Apr. 29, 2011, entitled ELECTROLYTE AND pH MONITORING FOR FLUID REMOVAL PROCESSES, which application is hereby incorporated herein by reference in its entirety to the extent that it does not conflict with the present disclosure. Of course, any suitable sensor or systems for monitoring pH and electrolyte concentration may be used. For example, a transducer may be employed to detect pH or electrolytes. Suitable transducers may include an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein. One or more sensors may be employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components. A sensor (or transducer) for detecting pH, electrolyte concentration, or the like may be placed at any suitable location for purposes of monitoring electrolytes or pH. For example, the sensor may be implanted in the patient, located external to the patient an upstream of a blood fluid removal device, located external to the patient and downstream of the blood fluid removal device, or the like.

Examples of sensors and systems for monitoring cardiovascular parameters are disclosed in U.S. Provisional Patent Application No. 61/480,535, filed on Apr. 29, 2011, entitled CARDIOVASCULAR MONITORING FOR FLUID REMOVAL PROCESSES, which application is hereby incorporated herein by reference in its entirety to the extent that it does not conflict with the present disclosure. Of course, any suitable sensor for monitoring cardiovascular parameters may be used. In embodiments, pH or electrolyte sensors; e.g., as described above, may be used to monitor cardiovascular parameters. Sensors for monitoring heart rate or heart rhythm may be used. One suitable implantable sensor device that is configured to monitor a patient's ECG signals is a Medtronic, Inc.'s Reveal® series insertable cardiac monitor. In embodiments, the sensor device may be a suitably equipped pacemaker or defibrillator already implanted in the patient. Monitored cardiac signals from such a device may be transmitted to a blood fluid removal device or intermediate device for use in the blood fluid removal session or for setting the prescription for the blood fluid removal session. Blood pressure monitors, which may be external or implantable (such as Medtronic Inc.'s active leadless pressure sensor (ALPS), which generally takes the form of a stent to anchor the device within a vessel, may be employed. Such a device may be placed in any suitable blood vessel location, such as in a femoral artery or pulmonary artery. A wearable sensor system, such as a Holter sensor system, may be used to monitor ECG activity of the patient. Regardless of whether the sensor or sensor system employed, or components thereof, is implantable, wearable, part of a larger stand-alone device, or part of a blood fluid monitoring device, the sensor may monitor any suitable cardiovascular parameter of a patient. In various embodiments, the sensors or monitoring systems are configured to monitor one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

As indicated above, sensors for monitoring patient physiological parameters may be, or may have components that are, implantable or wearable. In embodiments, multiple sensors may be connected via telemetry, body bus, or the like. The connected sensors may be of the same or different type (e.g., pH or impedance). Such connected sensors may be placed (e.g., internal or external) for purposes of monitoring at various locations of the patient's body.

Monitoring may occur during a blood removal session or between blood removal sessions. In embodiments, blood fluid removal is chronically performed, such as when a blood fluid removal device or a component thereof is wearable or implantable, and monitoring is chronically performed. Chronic monitoring in association with blood fluid removal is described in U.S. Provisional Patent Application No. 61/480,544, filed on Apr. 29, 2011, entitled CHRONIC pH OR ELECTROLYTE MONITORING, which application is hereby incorporated herein by reference in its entirety to the extent that it does not conflict with the present disclosure.

Monitoring may alternatively or additionally include receiving patient or physician feedback regarding the patient's state. For example, the patient may indicate a point in time when cramping begins, which often happens when too much fluid is removed. The blood fluid monitoring device may include an input, such as a keyboard or touch screen display for entering such data. Alternatively, a separate device such as a patient programmer, laptop computer, tablet computer, personal data assistance, smart phone or the like may be used to input the data; or the like.

Any suitable system variable 530 may be adjusted. FIGS. 10-15, and the associated text below, describe some suitable blood fluid removal systems and variables that may be adjusted. In many cases, fluid removal rate, blood flow rate, or concentration of electrolyte or composition of pH buffer in replacement fluid or dialysate may be adjusted. It may be desirable to monitor blood fluid removal system parameters to ensure that the system is performing in an expected manner. For example, it may be desirable to monitor fluid rate removal rather than merely adjusting a system variable related to fluid removal rate to ensure that the adjusted system variable actually adjusted the fluid removal rate in the expected manner. Any suitable system and method may be employed to monitor such system performance. Examples of systems and methods for monitoring system performance are described in U.S. Provisional Patent Application No. 61/480,541, filed on Apr. 29, 2011, entitled BLOOD FLUID REMOVAL SYSTEM PERFORMANCE MONITORING, which application is hereby incorporated herein by reference in its entirety to the extent that it does not conflict with the present disclosure. For example, flow sensors such as an acoustic Doppler velocimeter, an optical flow meter, a thermal flow meter, a Venturi meter, in-fluid paddle type meter, or the like may be used upstream or downstream of blood fluid removal device to monitor system performance. Sensors configured to monitor an indicator of a compound in blood or in fluid removed from the blood may be used to monitor system performance. The sensors may be configured to monitor components of blood that are configured to be removed during some blood fluid removal processes, such as hemodialysis. Examples of such compounds include urea, creatinine, sulfate, phosphate, $\beta$-2-microglobulin, or the like. Sensors capable of measuring such compounds are known in the art and can be readily adapted for used herein. For example, Nova Biomedical manufactures a variety of sensors capable of detecting components in blood such as creatinine, phosphate, urea and the like, which sensors can be employed or adapted for use herein. Other urea sensor detection technology that may be employed or adapted for used herein is described by Zhong et al., Clin. J. Biotechnol. 1992; 8(1):57-65. β-2-microglobulin sensor detection technology that may be employed or adapted for used herein is described by Brynda et al., Biosens Bioelectron. 1999; 14(4):363-8 and by Nedelkov et al., Proteomics. 2002; 2(4):441-6. Of course, any suitable sensor technology may be employed. By way of further example, pressure sensors may be employed to monitor pressure differential across a blood fluid removal membrane to monitor system performance.

Figure 2:
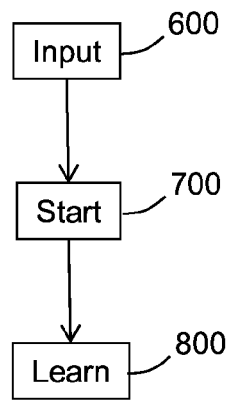

Referring now to FIG. 2, a high level flow diagram of a method is described. The method includes providing input (600), such as input variables discussed above with regard to FIG. 1, to a blood fluid removal system. The method also includes initiating or starting (700) a blood fluid removal session, and learning (800) from the session. The learning (800) may be as discussed above with regard to FIG. 1 with system parameters being varied and patient physiological parameters being monitored to determine which system parameter adjustments result in desirable patient physiologic outcomes.

Figure 3:
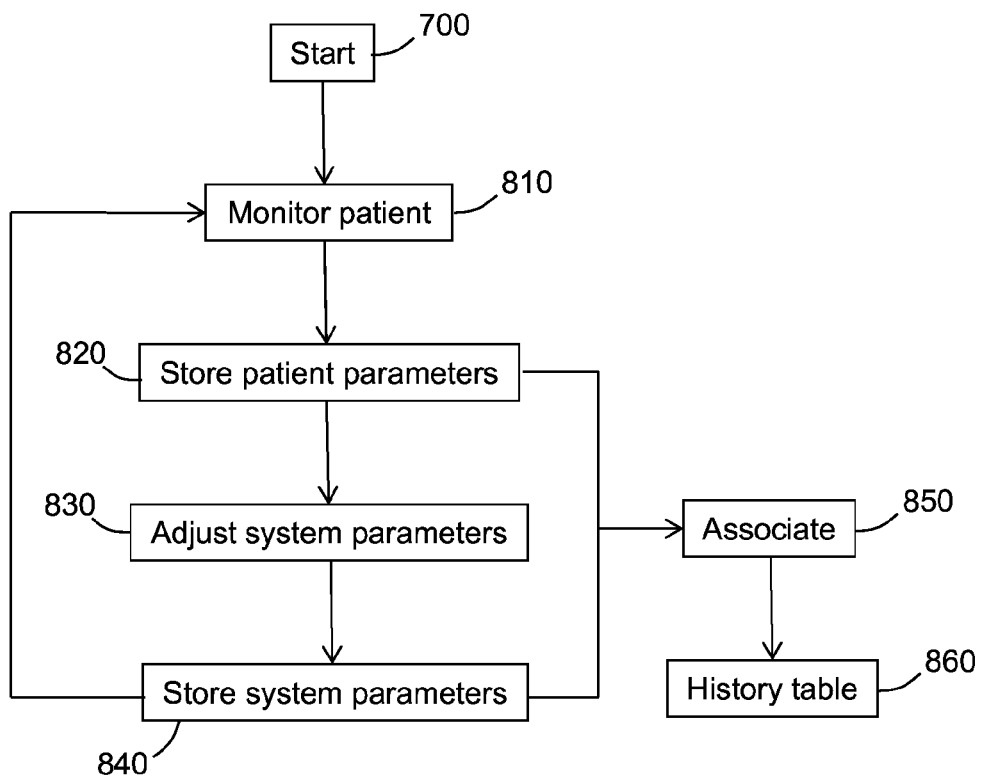

For example and with reference to FIG. 3, additional detail regarding an embodiment of a learning process that may occur during a blood fluid removal session is shown. The blood fluid removal session is started (700) and the patient is monitored (810). Monitored patient parameters, such as patient physiological variables as discussed above, are stored (820); e.g., in memory of the blood fluid removal system. The system parameters, such as system variables described above, which may include rate of fluid removal from the blood or electrolyte concentration of a dialysate or replacement fluid, are adjusted (830) and the system parameters are stored (840); e.g., in memory of the blood fluid removal system, and patient monitoring (810) continues. The set of stored patient parameters (820) are associated (850) with a set of stored system parameters (840) so that the system may recall particular system parameters that were employed at the time the patient had a given set of parameters. The data regarding the stored patient parameters (820) and the stored system parameters (840) may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to changing system parameters (860).

Figure 4:
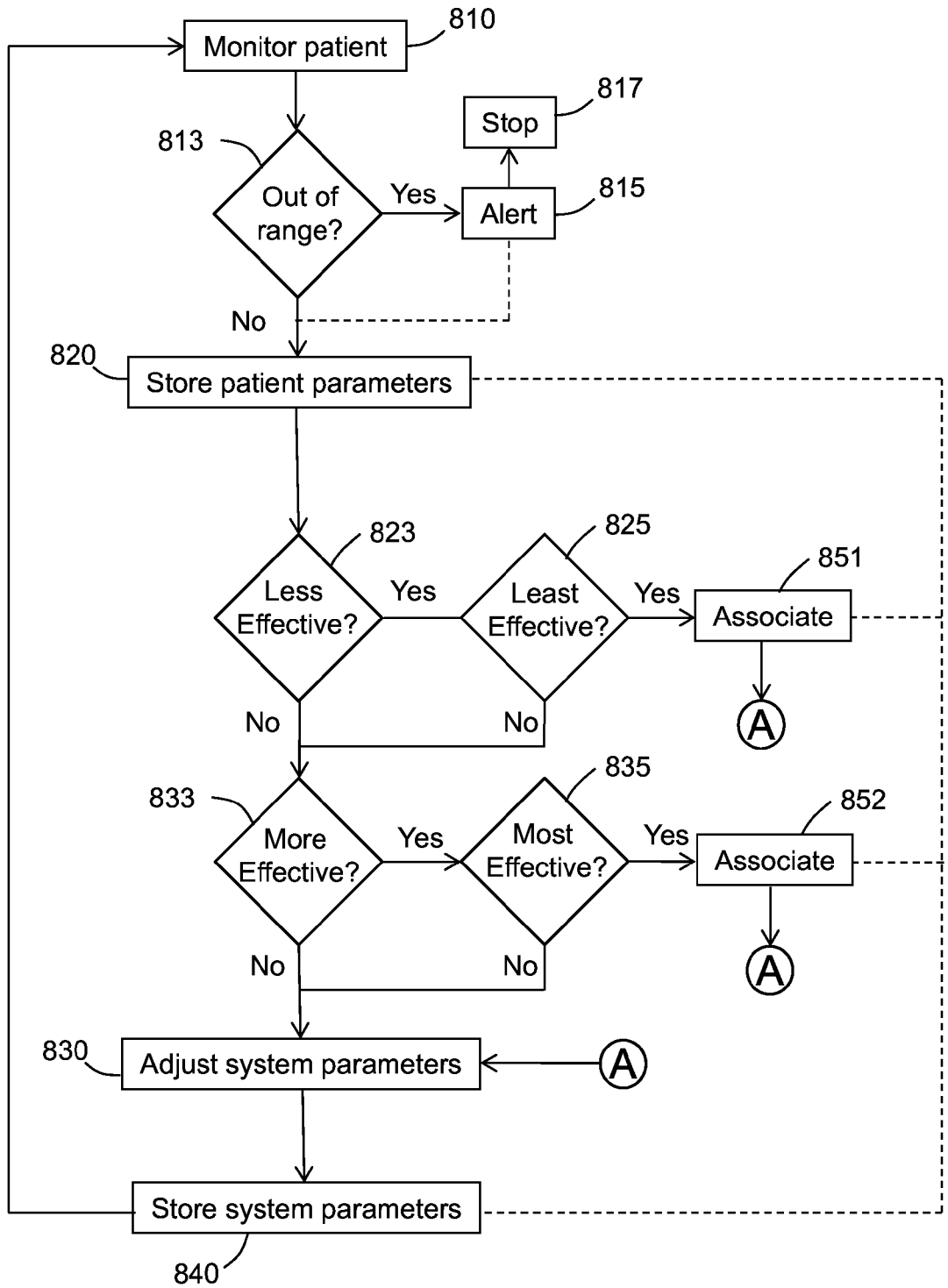

A more detailed embodiment is presented in FIG. 4. In the embodiment depicted in FIG. 4, patient is monitored (810) during a blood fluid removal session. It may be desirable to determine whether data acquired from patient monitoring is out of range (813). As used herein, "out of range" means that a value of a monitored parameter exceeds (ie., is above or below) a predetermined range of values. The predetermined range of values may be indicative of a patient safety concern. If the data is out of range, an alert may be issued (815) or the session may be stopped (817). In some cases, it may be desirable to continue with the session, even if the monitored data, or some aspect thereof is out of range. In the depicted embodiment, if the session is continued, (e.g., due to choice or to the monitored data not being out of range), data regarding the monitored patient parameters is stored (820) and is compared to stored patient data previously obtained (e.g., in a prior session or earlier in the session). A determination may be made as to whether the present patient data is less effective (823) than stored patient parameter data resulting from system parameter adjustments (830) that occurred just prior to the current set of system parameters. If the data is determined to be less effective (823), the stored current patient parameters (820) may be associated (851) with stored current system parameters (840); e.g., as discussed above. In some cases, it may be desirable to determine whether the current patient parameter data, or a portion or aspect thereof, is the least effective that has been detected in the patient in a current or previous blood fluid removal session (825); e.g. by comparing the current patient data to a history of collected patient data. If the current patient data is the least effective observed (825) to date, the stored current patient parameters (820) may be associated (851) with stored current system parameters (840). In this way, only the "least effective" patient conditions are tracked, as opposed to all patient conditions, which can save on memory and processing power. In any case, once the patient and system parameter data is associated (851), the system parameters may be adjusted (830) and the process repeated.

If the present patient parameter data is determined to not be less effective than stored patient parameter data resulting from system parameter adjustments that occurred just prior to the current set of system parameters, a determination may be made as to whether the present patient parameter data is more effective (833) than stored patient parameter data resulting from system parameter adjustments (830) that occurred just prior to the current set of system parameters. If the data is determined to be more effective (833), the stored current patient parameters (820) may be associated (852) with stored current system parameters (840); e.g., as discussed above. In some cases, it may be desirable to determine whether the current patient parameter data, or a portion or aspect thereof, is the most effective that has been detected in the patient in a current or previous blood fluid removal session (835); e.g. by comparing the current patient data to a history of collected patient data (e.g., "history table" in FIG. 3). If the current patient data is the most effective observed (835) to date, the stored current patient parameters (820) may be associated (852) with stored current system parameters (840). In this way, only the "best" or most effective patient conditions are tracked, as opposed to all patient conditions, which can save on memory and processing power. In any case, once the patient and system parameter data is associated (852), the system parameters may be adjusted (830) and the process repeated.

Figure 5:
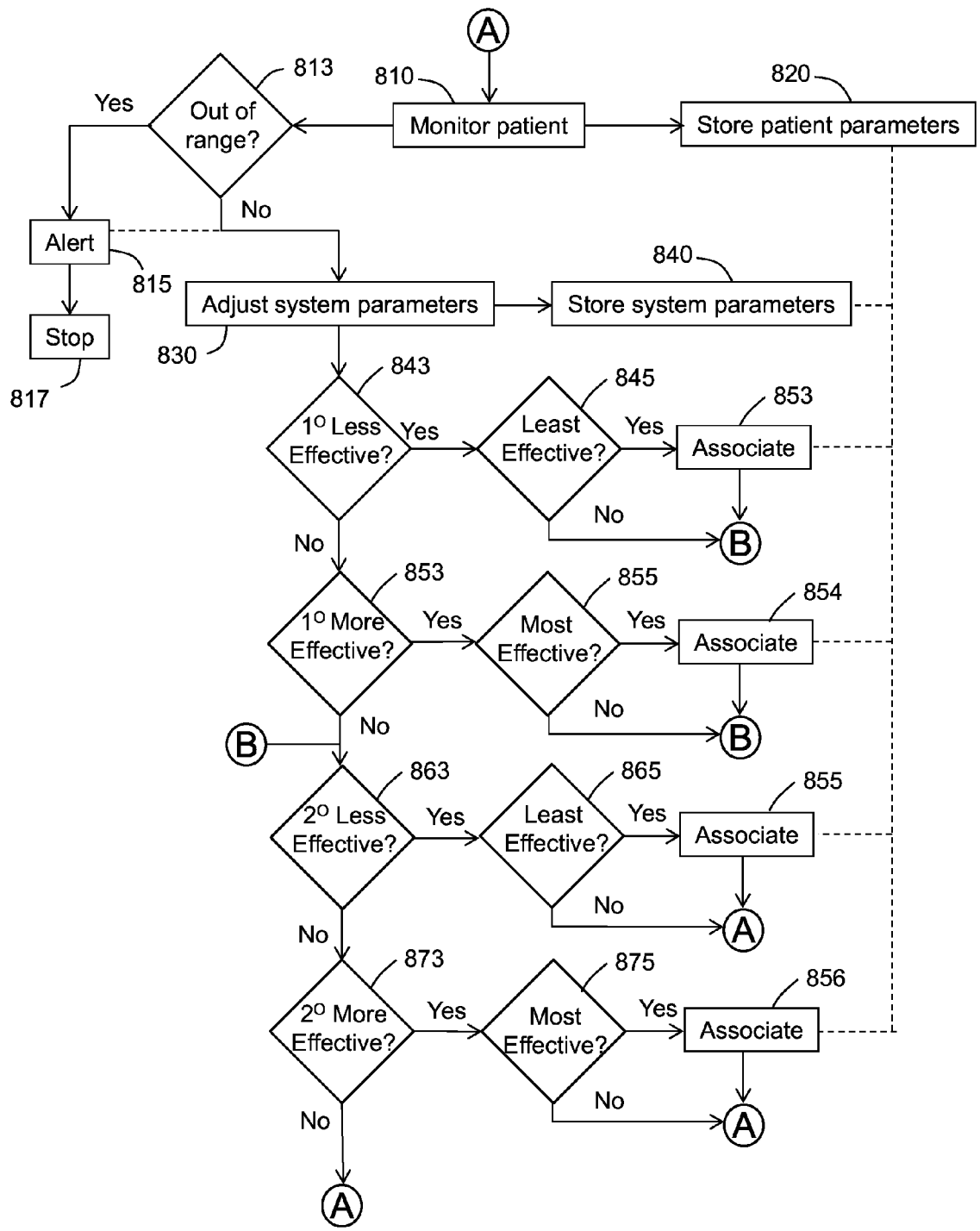

Referring now to FIG. 5, an embodiment of a method where more than one patient parameter variable is evaluated in a manner similar to that described with regard to FIG. 4. In the embodiment depicted in FIG. 5, two patient parameter variables are evaluated. However, it will be understood that any number of patient parameter variables may be evaluated by employing a method as depicted in FIG. 5 or using any other suitable method. In the embodiment depicted in FIG. 5, the variables are labeled "primary" and "secondary", as it may be desirable to prioritize patient parameter variables. For example, in some cases it may be desirable to monitor blood pressure and attempt to achieve a stable blood pressure at or near a target range throughout the session because hypotension is one of the most common side effects of blood fluid removal sessions. That is, as long as other patient parameters are not out of a pre-determined range, the system may attempt to keep blood pressure in check and make adjustments to that end. However, in some cases, reducing arrhythmias is the primary goal, as many patients for which a blood fluid removal process is indicated dire from complications due to arrhythmias. If arrhythmias are determined to be the primary patient parameter, the blood fluid removal system may attempt to keep arrhythmias in check and make adjustments to this effect without regard to other patient parameters, e.g., as long as the other patient parameters remain within acceptable limits.

The method depicted FIG. 5 includes monitoring patient parameters (810) (at least a primary and secondary patient parameter), storing patient parameter data (820), and determining whether a parameter, or aspect thereof, is out of a predetermined range (813). If the parameter is out of range, an alert may be issued (815), the blood fluid removal session may be stopped (817) or the session may continue. If the parameters are determined to not be out of range (813), the system parameters may be adjusted (843) and stored (840). A determination may then be made as to whether the primary patient parameter is less effective (843), e.g. by comparing current patient parameter data to stored patient parameter data resulting from system parameter adjustments that occurred just prior to the current set of system parameters. If the primary patient parameter is determined to be less effective (843), the current stored patient parameter data may be associated (853) with the current stored system parameters. Alternatively or in addition, a determination may be made as to whether the current patient parameter data regarding the primary parameter is the lease effective that has been detected in the patient in a current or previous blood fluid removal session (845); e.g., as discussed above with regard to FIG. 4. If it is the least effective, the current stored patient parameter data may be associated (853) with the current stored system parameters as described above with regard to FIG. 4. Similarly determinations as to whether the primary patent parameter data is more effective (853) or the most effective to date (855) may be made and stored system and patient parameters may be associated (854). Similar determinations regarding whether the secondary patient parameter, or a value associated therewith, is less effective (863), the least effective (865), more effective (873), the most effective (875) and appropriate associations (855, 856) may be made. In this manner, the system may identify and learn how system parameters may affect individually monitored patient parameters, such as blood pressure, heart rate, fluid volume, and electrolyte concentration. Based on this information, the system may make choices as to which system parameters may be employed to produce results that are likely to be favorable to the patient.

Figure 6:
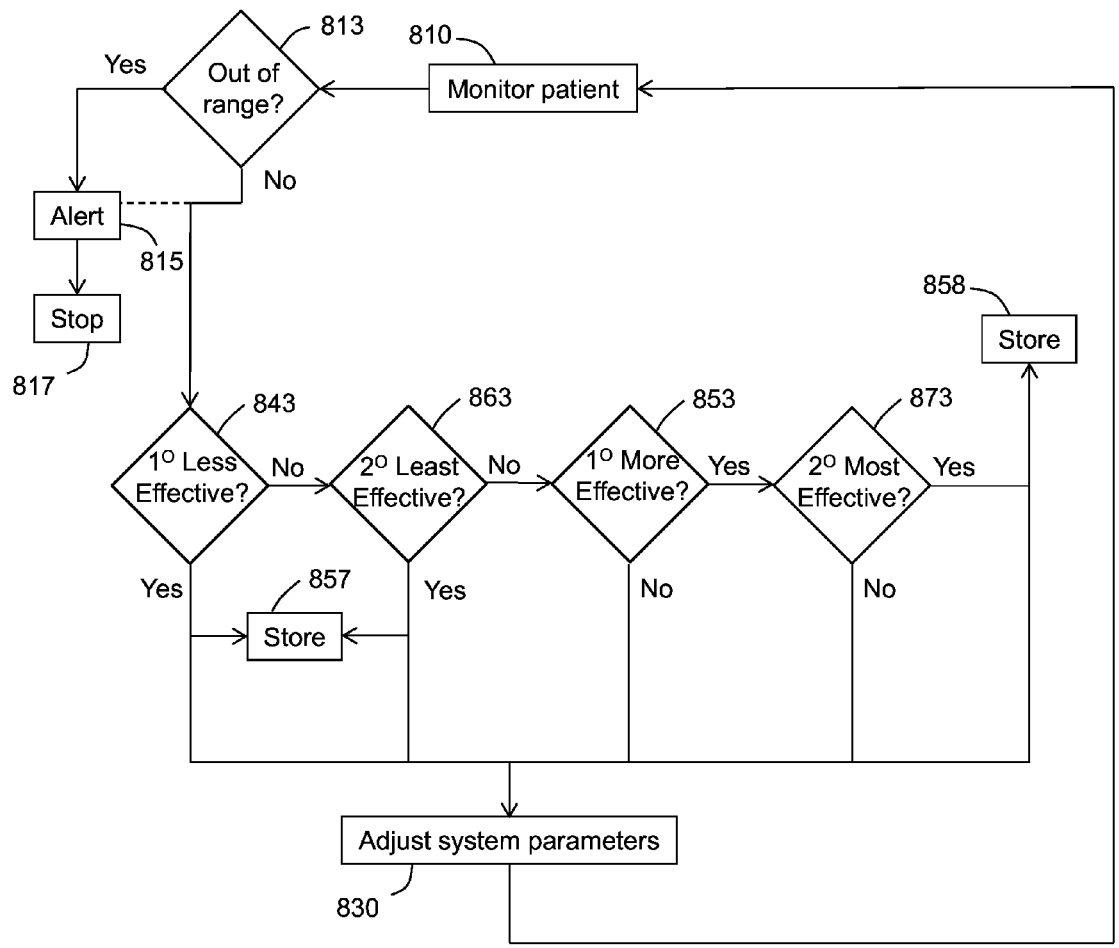

Referring now to FIG. 6, a flow diagram depicting a process where the combined response of two or more patient parameters to changes in system parameters (830) is tracked. For the purposes of convenience some of the steps depicted and described above with regard to FIGS. 4-5 are omitted from FIG. 6. However, it will be understood that the same or similar steps may be employed with regard to the method depicted in FIG. 6. In the depicted embodiment, patient parameters and system parameters are stored (857, 858) only when both the primary and secondary patient parameters are determined to become less effective (843, 863) or more effective (853,873). In this manner, the system may identify or learn which system parameters result in desirable (or undesirable) changes in multiple patient parameters.

Through the association of patient parameter data and system parameter data as shown in FIGS. 3-6 and discussed above, a history of patient responses to changing system parameters may be obtained. This history, which may be in the form of a lookup table, may be consulted prior to or during a blood fluid removal session to determine which system parameters, given the patient's physiological parameters at a given point in time, are more likely to cause the patient to respond favorably and which system parameters are more likely to cause the patient to respond negatively. Accordingly, the system may respond by adjusting parameters to those that are more likely to cause the patient to respond favorably.

Figure 7:
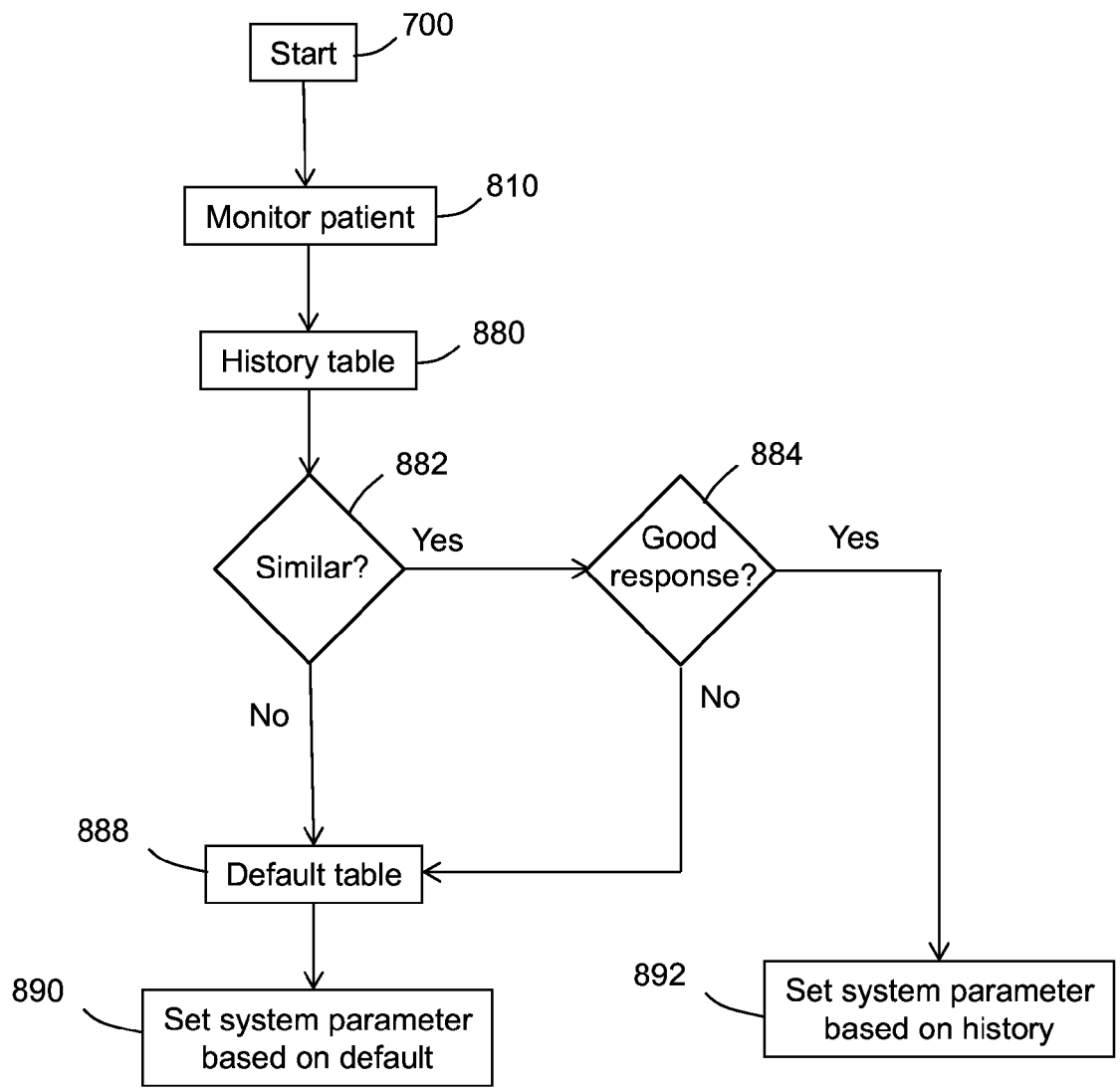

For example and with reference to FIG. 7, a flow diagram is shown that depicts and embodiment of how stored and associated data (e.g., as discussed above with regard to FIGS. 3-6) may be used to determine which system parameters to use at a given time in a blood fluid removal session. The method includes initiating or starting a blood fluid removal session (700), monitoring patient parameters (810), and consulting history lookup table (880), which may be generated by associating system parameters and patient parameters as described above with regard to FIGS. 3-6. A value associated with the current patient parameter data is compared to data regarding a corresponding value in the lookup table, and a determination is made as to whether the current patient parameter is similar to prior patient parameter data stored in the history table (882). By way of example, a value of a current patient parameter data set may be determined to be similar to a corresponding value in the lookup table if the values are within 10%. The system may scroll through the lookup table to identify the closest corresponding value, if more than one corresponding value is within the predetermined cutoff for being considered similar (e.g., within 10%). As used herein, a "corresponding" value is a value of the same parameter obtained at different times. The value may be a magnitude, a rate of change, an average, or the like. The parameter may be blood pressure, heart rate, fluid volume, concentration of electrolyte, or the like.

If more than one parameter or value of a parameter is compared to data in the lookup table, the system may determine whether each value for each parameter is within the predetermined cutoff for being considered similar and identify a prior patient parameter data set as being most similar by prioritizing or weighting parameters or by summing the percent differences between all of the current values and the corresponding values in the lookup table. Regardless of how the system determines whether a current patient parameter data set is similar, or most similar, to a prior patient data set stored in the history table, a determination may be made as to whether the patient's response to the system parameters associated with the stored patient parameter data table was a favorable response (884); e.g., was "better" (or "more effective") or "best" (or "most effective") as discussed above with regard to FIGS. 4-6. If the prior patient response was determined to be a good or "effective" response, the current system parameters may be set according to the parameters stored in the lookup table (892). If the prior patient response was considered to not to be similar (882) or effective (884), a default table may be consulted (888) which contains non-patient specific system parameters that would generally be considered suitable in general circumstances or that would be considered suitable for a patient presenting with the current physiological parameters. The system parameters may then be set according to the parameters stored in the default table (890).

It will be understood that prior patient negative responses (e.g., "less effective", "least effective") may be stored in a lookup table, accessed and used in a similar manner to that described with regard to the "effective" responses in FIG. 7. In some embodiments, separate lookup tables are maintained for "effective" responses (e.g., an "increased effectiveness" data table) and for "ineffective responses" (e.g., a "decreased effectiveness" data table). In some embodiments, the "increased effectiveness" lookup table and the "decreased effectiveness" lookup table are the same data table, which stores patient parameters and associated system parameters that resulted in "more effective", "most effective", "less effective" or "least effective" patient parameters.

Figure 8:
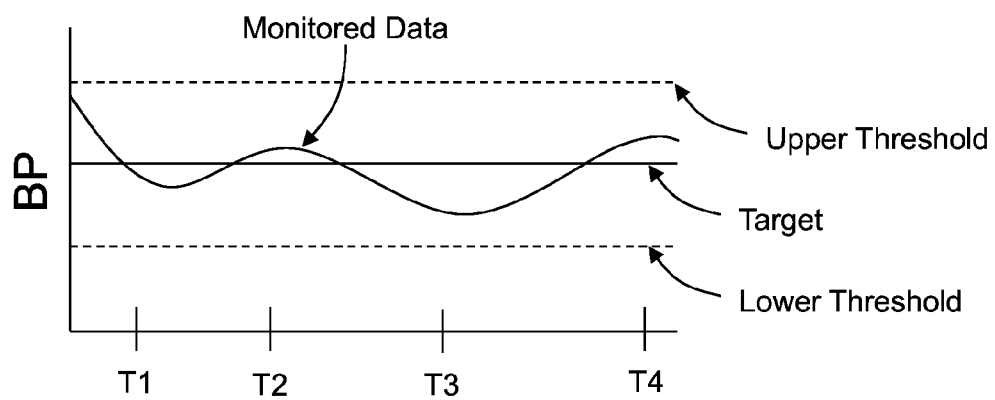
FIG. 8 is a schematic graphical representation of monitored data (not actual data) shown for purposes of illustration.
Figure 8:
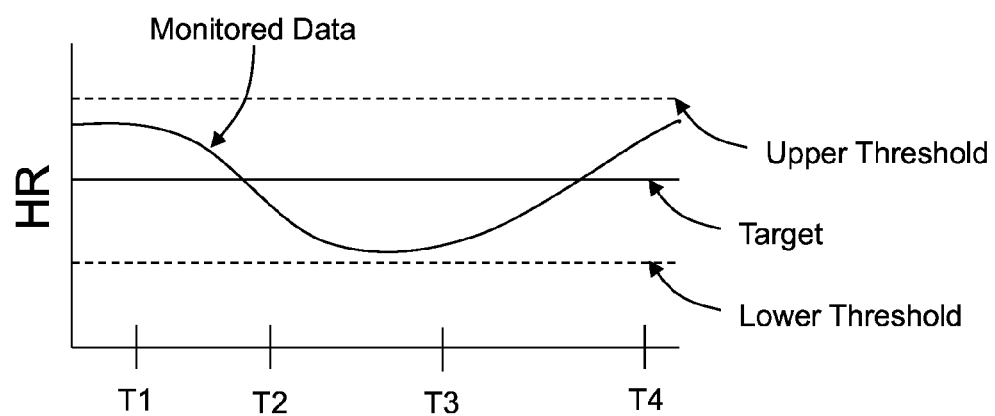
Figure 8:
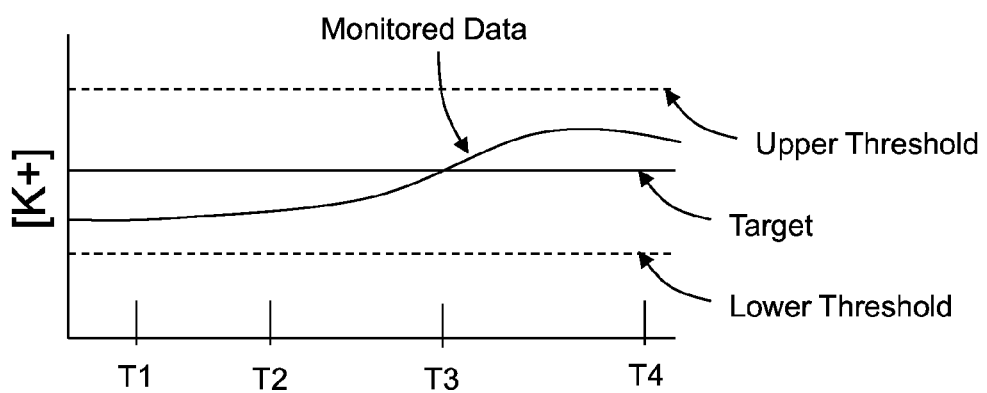

For purposes of example and to provide some clarity with regard to how one (or a blood fluid removal system) may determine whether patient parameter data is "out of range", "more effective", "less effective", and the like (as discussed above with regard to FIGS. 4-6), graphical schematic data is presented in FIG. 8 showing representations of monitored data (not actual data) for blood pressure (BP), heart rate (HR), and potassium concentration in the patient's blood ([K$^+$]). In the schematic illustration, system parameters are changed at times T1, T2, T3 and T4. The patient parameters (BP, HR, [K$^+$]) are shown as changing in response to the changes in blood fluid removal system parameters. As shown, not all patient parameters will respond similarly (e.g., more effective or less effective) in response to a system parameter change. In the depicted schematic illustrations, a desired target value is shown for each patient parameter. If the monitored data value achieves or approaches the target, a determination may be made that the change in system parameter resulted in an improvement or "more effective" state for that parameter. If the monitored data value deviates from the target, a determination may be made that the change in system parameter resulted in a worsening or "less effective" state for that parameter. It will be understood that the timing of the patient parameter response to a change in system parameters may vary greatly from patient parameter to patient parameter. In some cases, changes in a patient parameter may be observed within seconds or minutes of a change in a system parameter. In other cases, a change in a patient parameter in response to a change in a system parameter may take hours or more to be fully appreciated or observed.

In the graphical depictions of the represented monitored data presented in FIG. 8, a lower threshold value and an upper threshold value are depicted by horizontal dashed lines. If the monitored data for a patient parameter exceeds the upper threshold value or crosses below the lower threshold value, a determination may be made that the value for that parameter is "out of range."

It will be understood that the condition of a patient may deteriorate with time, which is typical of patients having chronic kidney disease. Accordingly, the targets and upper and lower thresholds may vary with time. These targets and thresholds may be modified by input from, for example, a healthcare provider from time to time based on, e.g., the patient's health or status of patient parameters. Alternatively, the system may automatically adjust target or threshold values over time based on population data or based on data of a particular patient indicative of a generally deteriorating condition. If the target or thresholds are adjusted to or near predetermined cutoff values, an alert may be issued to that effect.

Further, target and threshold values for one or more parameters may be modified on a session-by-session basis. For example, if the patient is excessively fluid overloaded prior to a given session, the target or threshold tissue fluid levels may be adjusted upward for the next or current session. The negative consequences of too much fluid removal in one session or at too fast of a rate may outweigh the negative consequences of higher fluid levels remaining in the patient. Additional or more frequent fluid removal sessions may be employed to return the patient to more desirable fluid levels.

As shown in the examples presented in FIG. 8, the patient parameters change over time. In embodiments, values of one or more patient parameters are averaged over a period of time to account for fluctuations that may occur. The averaged value may be compared to the target and thresholds for determining whether a patient is improving. By averaging values over time, the effect of an anomalous value that may deviate significantly from the target value or may be out of bounds may be diminished. Of course, thresholds may be set for single occurrences, for example if the values of those occurrences may present an imminent health concern to the patient. In embodiments, the presence a single occurrence that deviates significantly from other recent occurrences may result in activation of a subroutine or monitoring method for detecting similar subsequent deviations. In embodiments, consecutive significant deviations, a percent of significant deviations within a given number of samples, or the like, may result in activation or an alert or alarm.

In embodiments, patient parameters are measured or monitored within discrete windows of time rather than continuously. Such time sampling may be valuable for implantable systems or systems having implantable components as the power and processing requirements may be reduced relative to continuous monitoring.

The discussion with regard to FIGS. 3-8 has been primarily directed to blood fluid removal systems and processes that may occur during a blood fluid removal session for associating system parameter data and patient parameter data to enhance the blood fluid removal session or to tailor the blood fluid removal treatments to render the treatment patient-specific. It will be understood that any suitable method or process may be employed to achieve such results, and such methods or processes are contemplated for use herein. It will be further understood that similar methods or processes may be employed to enhance or tailor system parameters prior to initiating a blood fluid removal session so that patient-specific parameters may be set at the beginning of a session.

Figure 9:
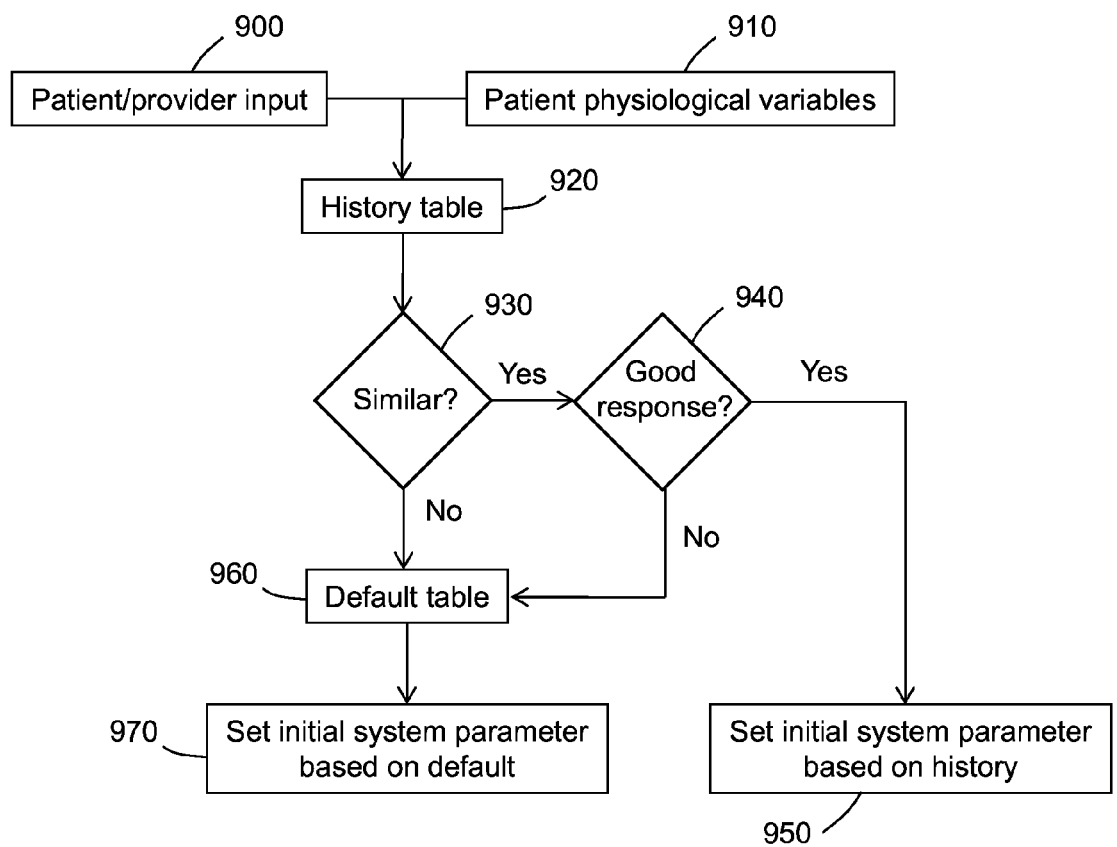
FIG. 9 is a flow diagram illustrating an embodiment of a method described herein.

For example and with reference to FIG. 9, a flow diagram depicting a method that may be employed to determine which system parameters to select at the beginning of a blood fluid removal session is shown. The depicted method is similar in many respects to the method depicted in FIG. 7. In FIG. 9, the method includes receiving, inputting or obtaining patient or physician input (900) and patient physiological parameters (910). As discussed above with regard to FIG. 1, physician or patient input may include how long since the patient's last blood fluid removal session, how long does the patient have for the given blood fluid removal session and the like. In some embodiments, system generated input is provided based on data collected during the last session. Patient physiological parameters may be similar to those described above. A history lookup table may be consulted (920), and a determination may be made as to whether the patient has previously come to a blood fluid removal session in a similar state (930) based on the patient or physician input, the patient's physiological parameters, or other input. If a determination is made that the patient has come to previous blood fluid removal session in a similar state (930), which decision may be made generally as described above with regard to FIG. 7, a determination may be made as to whether system parameters were used in such a previous session to which the patient responded to favorably or had an "effective" response (940). If the patient is determined to have had an effective response, then the initial system parameters may be set in accordance with the parameters stored in the history table (950). If the patient is determined to not have come to a blood fluid removal session in a similar state (930) or to not have had an effective response (940), then a default table (e.g., similar to as described above with regard to FIG. 7) may be consulted (960) and the initial system parameters may be set according to the parameters in the default table (970).

It will be understood that the processes, and components thereof, described above with regard to FIGS. 1-7 and 9 are provided for purposes of illustration and not limitation. Process steps other than those described herein, or derivations of the steps or components to carry out the steps, may be employed. Further, process steps depicted and discussed above may be interchanged, substituted, added to, or omitted from processes of alternative embodiments, as appropriate.

The processes described above may be employed with any suitable device or system for removing fluid, or fluid and contaminants, from blood. The devices, or components thereof, may be traditional large counsel-type, wearable, or implantable.

Figure 10:
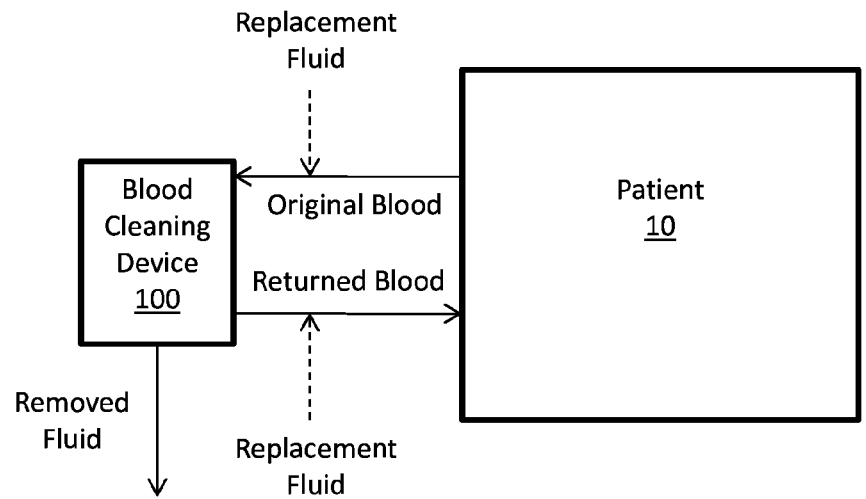
FIGS. 10-12 are schematic block diagrams showing interaction of blood fluid removal devices with a patient showing flow of blood (dashed arrows) and fluid (solid arrows), which blood fluid removal devices may be used in various embodiments described herein.
Figure 11:
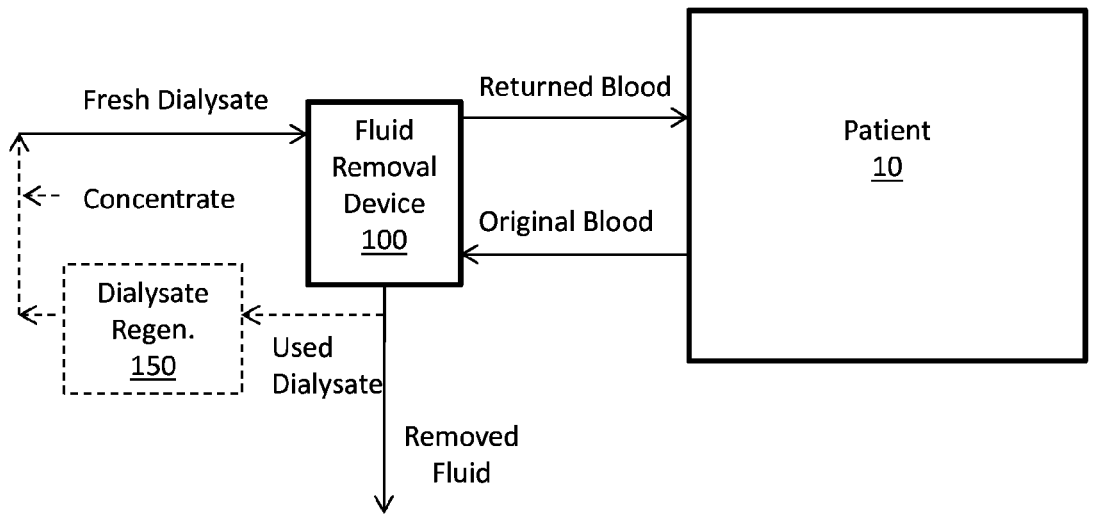
Figure 12:
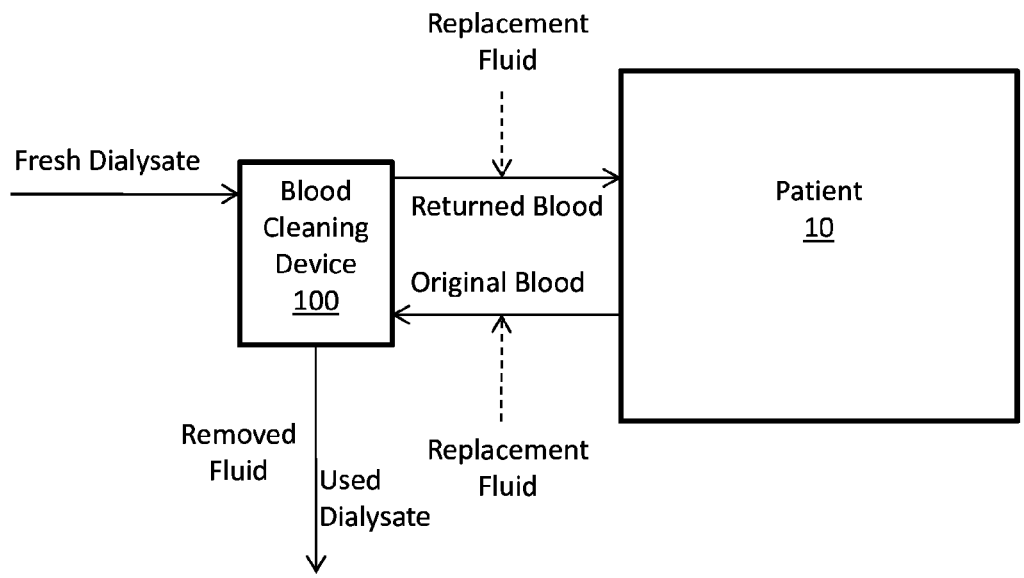

Block diagrams of some example devices and systems are shown in FIGS. 10-12. As shown in FIG. 10, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 10 are ultrafiltration and hemofiltration devices. Examples of such devices and components thereof that may be employed in accordance with the teachings presented herein are well known in the art. With some of such devices, replacement fluid may be introduced into the patient's blood if fluid is removed from the blood by the device 100 at too great of a rate or amount. The replacement fluid may be added to the original blood before fluid removal or may be added to the blood after initial fluid removal and prior to return to the patient's cardiovascular system. Preferably, the replacement fluid is added after initial fluid removal. The pH and electrolyte concentration of the replacement fluid may be set or adjusted, e.g. as described in more detail below.

As shown in the embodiment depicted in FIG. 11, the blood fluid removal device 100 may employ dialysate to assist in removal of contaminants from the patient's blood and in maintaining proper pH and electrolyte balance. The pH or electrolyte concentration of the dialysate may be set or adjusted, e.g. as described in more detail below. Used dialysate and fluid removed from the blood may be diverted. In some embodiments, particularly where the blood fluid removal device 100 or system or components thereof are wearable or implantable, the used dialysate and removed fluid, or a portion thereof, may be regenerated (indicated by dashed lined regeneration system 150) to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. As shown in FIG. 11, a concentrate may be added to the regenerated dialysate to adjust the pH and electrolytes of the regenerated dialysate to an amount suitable for re-use as fresh dialysate.

Regardless of whether the dialysate is regenerated, systems and devices that operate in a manner shown in the embodiment of FIG. 11 include hemodialysis and hemodiafiltration systems. Examples of such devices and components thereof that may be employed in accordance with the teachings presented herein are well known in the art. It will be understood that peritoneal dialysis, where the dialysate is introduced into peritoneal cavity may also be employed.

As shown in FIG. 12, in cases where the blood fluid removal device 100 of FIG. 11 removes fluid from the blood at too high of a rate, replacement fluid may be introduced into the patient's blood, upstream or downstream of fluid removal, e.g. as described above with regard to FIG. 10.

Regardless of the device or blood fluid removal process employed, system parameters such as rate of fluid removal, blood flow rate or electrolyte or pH buffer component or concentration may be controlled. Some schematic block diagrams for controlling electrolyte or pH of a dialysate or replacement fluid (and thus of blood) are shown in FIG. 13, in which representative components of an example of a closed-loop system for adjusting pH and electrolyte concentrations of fluid are shown.

Figure 13:
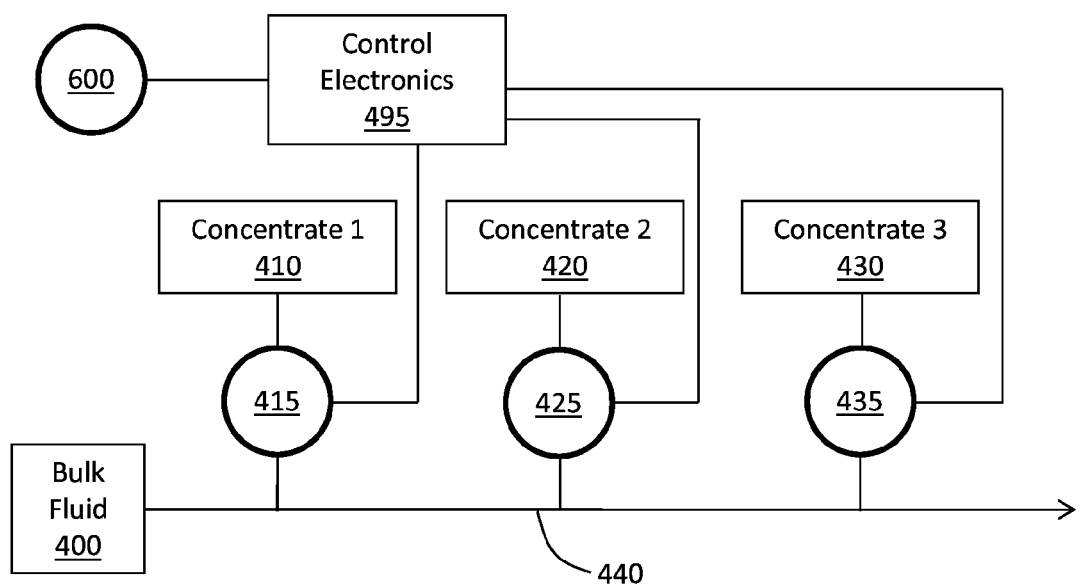
FIG. 13 is a schematic block diagram showing flow paths and some control mechanisms for controlling flow of concentrate into fluid for use in a blood fluid removal process.

With reference to FIG. 13, input data 600 (e.g. input 600 as discussed above with regard to FIG. 2) or "learned" parameters may be presented to, or processed within, control electronics 495, which are configured to control flow control elements 415, 425, 435, such as valves. The electronically controllable flow control elements 415, 425, 435 are in fluid communication with supplies of concentrated electrolyte or buffer solutions 410, 420, 430 and with fluid line 440, which may be a catheter for carrying fresh dialysate or a catheter for carrying replacement fluid. The electronically controllable flow control elements 415, 425, 435, via control electronics 495, control the rate at which the concentrates 410, 420, 430 flow into the fluid line 440. The concentrates 410, 420, 430 are added to bulk fluid 400 to adjust the concentration of electrolytes or the pH of the bulk fluid (and thus the blood).

Any number of suitable concentrates may be used. For example, one concentrate may be sufficient with higher amounts being added when the electrolytes are determined to be low in the patient's blood, and smaller amounts being added when the electrolytes are determined to be high in the patient's blood. More than one concentrate may be used when it is desired to, for example, control pH and electrolyte concentration independently or to control concentration of different electrolytes independently.

Control elements 415, 425, 435, as depicted in FIG. 13 and discussed above, may be any suitable control element, such as electronically controllable valves, electronically controllable pump mechanisms, or the like.

Any suitable system may be configured as depicted in FIG. 13 to provide control of adjustment of pH or electrolytes based on input data 600 or "learned" parameters. By way of example, selected components of two example systems are illustrated in FIGS. 14-15.

Figure 14:
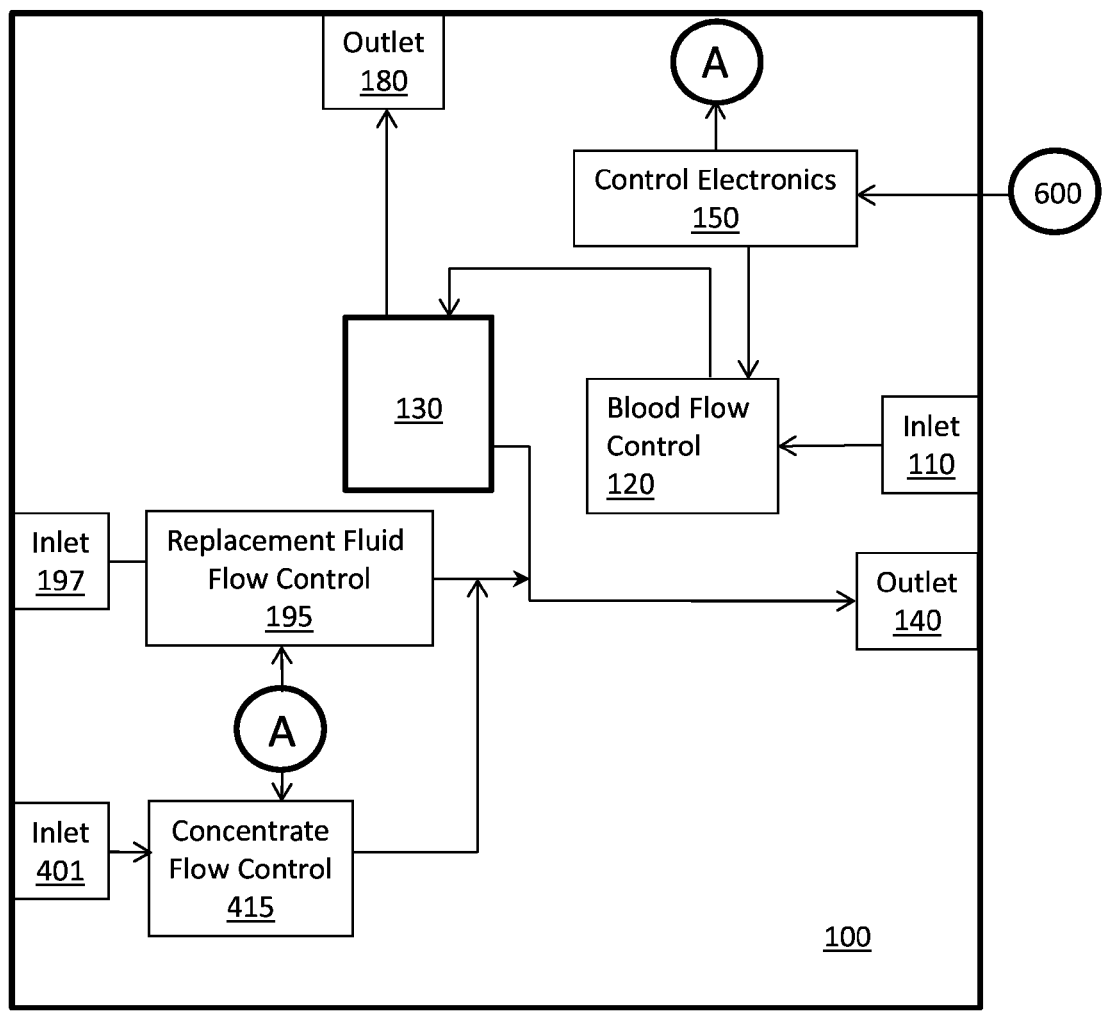
FIGS. 14-15 are schematic block diagrams of some components of blood fluid removal devices that are configured to various system parameters.
Figure 15:
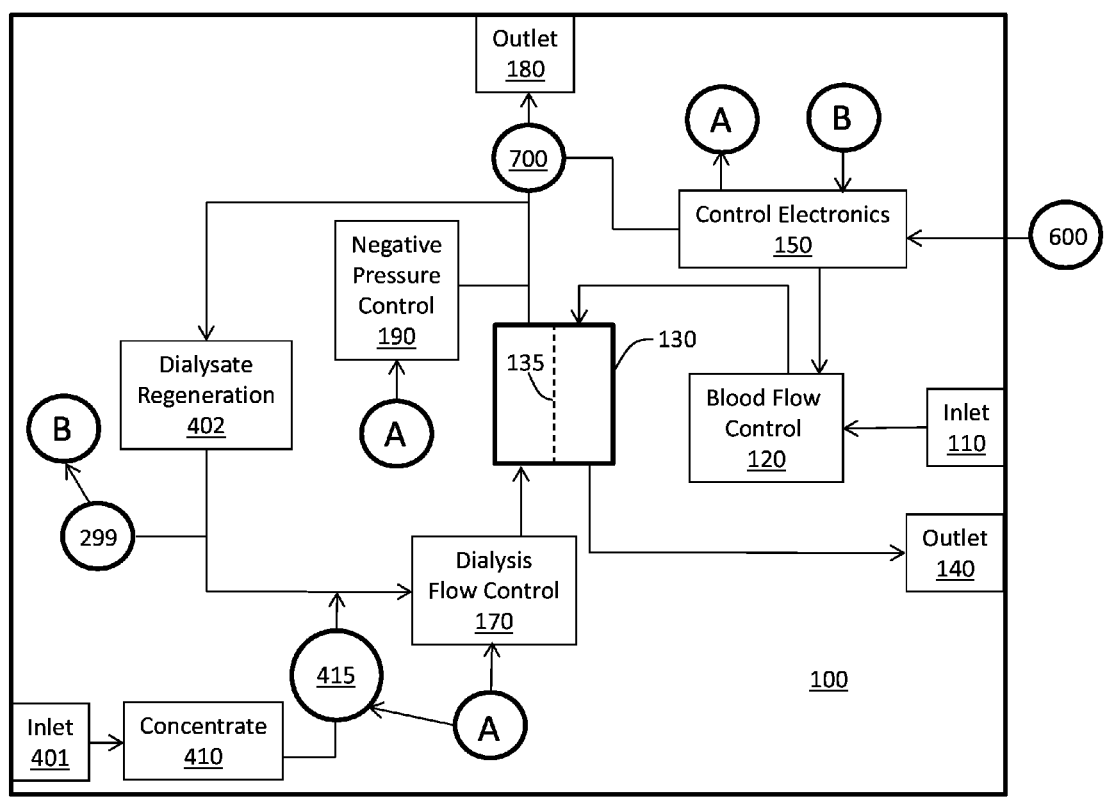

Referring now to FIG. 14, the depicted device 100 includes a fluid pathway for adding replacement fluid to blood before it is returned to the patient. The device 100 includes an inlet 110 for receiving blood from the patient and an outlet 140 for returning blood to the patient. In the flow path between the inlet 110 and outlet 140 are a blood flow control element 120 and a medium for removing fluid and contaminants from the blood. The blood flow control element 120 is operably coupled to control electronics 150 which provide instructions to control the rate at which blood is passed through medium 130. Fluids and contaminants removed from the blood by the medium 130 may exit via outlet 180.

The device 100 depicted in FIG. 14 also includes an inlet 197 for receiving bulk replacement fluid and a replacement fluid flow control element 195 in communication with the inlet and configured to control the rate at which the replacement fluid is added to the blood. The control electronics 150 are operably coupled to the replacement fluid flow control element 195 and are configured to control the rate at which replacement fluid flow control element 195 adds fluid to the blood. The device 100 also includes (i) an inlet 401 for receiving a concentrate for adjusting the pH or electrolyte concentration of the bulk replacement fluid, and (ii) a concentrate flow control element 415 in communication with the inlet 401 and configured to control the rate at which the concentrate is added to the replacement fluid or blood before the blood is returned to the patient. Preferably, the concentrate is added to the replacement fluid prior to the replacement fluid being added to the blood (as depicted) so that the concentrate may be mixed or diluted prior to being added to the blood. The device may include a mixer (not shown) to mix the concentrate and bulk replacement fluid prior to adding to the blood.

In the device depicted in FIG. 14, the control electronics 150 are operably coupled to the concentrate flow control element 415 and are configured to control the rate at which the concentrate flow control element 415 adds fluid to the replacement fluid or blood. By controlling the rate at which the concentrate is introduced into replacement fluid or blood, the concentration or pH (or buffering capacity) of the returned blood can be controlled.

Referring now to FIG. 15, in which components that are numbered the same as in FIG. 14 refer to the same or similar components, a schematic block diagram of selected components of a blood fluid removal device 100 is shown. In the embodiment depicted in FIG. 15, the device has in inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 includes a semipermeable filter 135, such as a hemodialysis or hemodiafiltration filter. The membrane separates a blood flow compartment from a dialysis flow compartment of the medium component 130.

In the embodiment depicted in FIG. 15, used dialysate is regenerated by passing through dialysate regeneration medium 402 or components, such REDY regeneration medium and components, or the like, to regenerate bulk dialysate. The device also has an outlet 180 in communication with the medium 130 for diverting fluid removed from the blood out of the device. A flow regulator element 700, such as a valve, is operably coupled to control electronics 150 and is disposed in the flow path between the medium 130 and the outlet 180 to control the amount of fluid that exits the device (as a portion of the fluid is regenerated). Often, the regeneration media or components (402) remove much of the pH buffer or electrolytes from the dialysate. Accordingly, a concentrate containing concentrated electrolytes and pH buffers is added to the regenerated dialysate before the dialysate re-enters the medium 130. In some embodiments, a sensor 299 is positioned downstream of the regeneration medium 402 to monitor a level of a component of the regenerated dialysate. The sensor 299 may be a pH or electrolyte sensor and data acquired from sensor 299 may be used in determining how much concentrate to add to the regenerated fluid (which data may be provided to control electronics 150). The sensor 299 may be a sensor that monitors a blood waste product, such as urea, to determine whether the regeneration media 402 is properly functioning. Increased or detectable levels of a waste product may indicate that the regeneration media 402 or components may need replacement or regeneration.

In the depicted embodiment, the concentrate 410 is stored in a reservoir 410, having an inlet 401 that allows the concentrate supply in the reservoir 410 to be replenished from time to time. The rate at which the concentrate is added to the regenerated dialysate is controlled by concentrate flow control element 415, which is operably coupled to control electronics 150, and may be based on input data 600 or "learned" parameters as described above.

The device 100 in FIG. 15 also has a dialysis flow control element 170 for controlling the rate at which dialysis is introduced into the dialysis flow compartment of the medium 130.

In the depicted embodiment, the device 100 also includes a negative pressure control element 190 in communication with the dialysate compartment of the medium component 130. The negative pressure control element 190, which may include a vacuum pump or the like, may be used to generate or change a pressure differential across the membrane to control the rate at which fluid is removed from blood that passes though the medium component 130.

The control electronics 150, which may include a processor, memory, etc., are operably coupled to, and configured to control, the blood flow control element 120, the dialysis flow control element 170, and the negative pressure control element 190. By controlling these elements in a coordinated manner, the rate at which fluid is removed from blood may be controlled. It will be understood that a device 100 need not have all of the controllable elements (120, 170, 190) depicted in FIG. 15 to effectively control rate of fluid removal from blood.

Any suitable control element may be used for the various control elements (120, 150, 170, 195, 415) depicted in FIGS. 14-15. For example, a variable or adjustable rate pump may be employed. Alternatively or in addition, a series of electronically controllable valves may be employed. In some embodiments, the valves are in communication flow paths having differing flow resistances.

While FIGS. 14-15 depict components as being within a single unit, it will be understood that one or more of the components may be housed in separate units. For example, the control electronics, or a portion thereof, may be housed in a separate device, such as a computer, tablet, physician programmer, or the like. The computer, tablet, etc. may receive input from sensors, determine appropriate action to take, and instruct appropriate components of a blood fluid removal device to take the appropriate action.

It will be understood that the blood fluid removal devices and systems, and components thereof, described herein are presented for purposes of illustration and not limitation. Components, devices and systems other than those described herein, or derivations of the components, devices and systems described herein, may be employed. Further, components of the devices depicted and discussed above may be interchanged, substituted or added to components of alternative embodiments, as appropriate. Further, it will be understood that, while many of the blood fluid removal devices depicted in a variety of the figures, such as FIGS. 10-12, are shown as external to the patient, the teachings presented herein apply if the device, or components thereof, were implanted in the patient.

The devices and systems described above, or components thereof, may be used to carry out the methods depicted in FIGS. 1-7 and 9, or portions thereof. Of course, any suitable device or system may be employed to carry out the methods, or portions thereof, described above.

The methods described herein, including the methods depicted in FIGS. 1-7 and 9, may be carried out by blood fluid removal devices or systems, or other devices in communication with blood fluid removal devices or systems. These methods may be algorithms or instructions programmed into memory of such devices, which may be carried out by processors or other control electronics of the devices. Preferably, the processor is in communication with appropriate control elements of the devices and is configured to control such elements in a manner such that the programmed instructions are carried out by the appropriate device. It will be understood that a computer readable medium programmed with instructions that cause a sensor device, blood fluid removal device, or other suitable device to carry out a method, or a portion thereof, as described herein are contemplated. The computer readable medium may be non-transitory, i.e. lasting for more than a fleeting instant or seconds. The medium may be memory, such as RAM or ROM, a cd or dvd, flash memory, or the like.

Various aspects of methods, devices, systems, computer-readable media, and the like are described herein. A summary of some of selected aspects described herein is presented below.

In a first aspect, a method carried out by a blood fluid removal system, comprises (a) initiating a blood fluid removal session with initial system parameters; (b) acquiring a first set of data regarding one or more patient physiological parameters; (c) storing the first data set in a most effective to date data set memory; (d) associating the initial system parameters in an increased effectiveness lookup table with the first data set; (e) adjusting at least one parameter of the blood fluid removal session to arrive at adjusted system parameters; (f) acquiring a second set of data regarding the one or more patient physiological parameters after the at least one parameter of the blood fluid removal session has been adjusted; and if at least one value of the second data set is closer to the target value than a corresponding at least one value of the first data set: replacing the first data set in the most effective to date data set memory with the second data set; storing in the increased effectiveness lookup table data regarding the second data set; and associating data regarding the adjusted system parameters with the second data set.

A second aspect is a method of the first aspect, further comprising (a) storing the first data set in a least effective to date data set memory; (b) associating the initial system parameters in a decreased effectiveness lookup table with the first data set prior to adjusting the at least one parameter of the blood fluid removal session; and (c) if the at least one value of the second data set is not closer to the target value than the corresponding at least one value of the first data set: replacing the first data set in the least effective to date data set memory with the second data set; storing in the decreased effectiveness lookup table data regarding the second data set; and associating data regarding the adjusted system parameters with the second data set.

A third aspect is a method of the first or second aspect, further comprising (a) further adjusting at least one parameter of the blood fluid removal session to arrive at further adjusted system parameters; (b) acquiring a third set of data regarding the one or more patient physiological parameters after the at least one parameter of the blood fluid removal session has been further adjusted; and (c) if at least one value of the third data set is closer to the target value than a corresponding at least one value stored in the most effective to date data set memory: replacing the data set in the most effective to date data set memory with the third data set; and storing in the increased effectiveness lookup table data regarding the third data set and associating data regarding the further adjusted system parameters with the third data set.

A fourth aspect is a method of the second aspect, further comprising (a) further adjusting at least one parameter of the blood fluid removal session to arrive at further adjusted system parameters; (b) acquiring a fourth set of data regarding the one or more patient physiological parameters after the at least one parameter of the blood fluid removal session has been further adjusted; and (c) if at least one value of the fourth data set is not closer to the target value than a corresponding at least one value stored in the least effective to date data set memory: replacing the data set in the least effective to date data set memory with the fourth data set; and storing in the decreased effectiveness lookup table data regarding the fourth data set and associating data regarding the further adjusted system parameters with the fourth data set.

A fifth aspect is a method of any of aspects 1-4, further comprising (a) acquiring a fifth set of data regarding one or more patient physiological parameters; (b) comparing the fifth data set to the increased effectiveness lookup table; and (c) adjusting the system parameters the system parameters associated with the data set stored in the increased effectiveness lookup table if at least one parameter of a data set stored in the increased effectiveness lookup table is within a predetermined range of the fifth data set.

A sixth aspect is a method of any of aspects 1-5, further comprising (a) stopping the blood fluid removal session; (b) acquiring a sixth set of data regarding one or more patient physiological parameters; (c) comparing the sixth data set to the increased effectiveness lookup table; and (d) initiating a second blood fluid removal session with the system parameters associated with the data set stored in the increased effectiveness lookup table if at least one parameter of a data set stored in the increased effectiveness lookup table is within a predetermined range of at least one parameter of the sixth data set.

A seventh aspect is a method of any of aspects 1-6, wherein the at least one of the one or more patient parameters are selected from the group consisting of blood pressure, heart rate, pH and concentration of an electrolyte.

An eighth aspect is a method of the seventh aspect, wherein the electrolyte is potassium.

A ninth aspect is a method of any of aspects 1-7, wherein the system parameters comprise one or more of fluid removal rate and concentration of one or more electrolyte.

A tenth aspect is a blood fluid removal system, comprising (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (e) control electronics comprising memory and a processor, wherein the control electronics are in operable communication with the one or more sensors and are operably coupled to the one or more control elements, wherein the control electronics are configured to carry out a method according to any of aspects 1-9.

An eleventh aspect is a system of the tenth aspect, wherein the blood fluid removal medium and the control electronics are housed within a blood fluid removal device.

A twelfth aspect is a system of aspect 10 of 11, further comprising a computer readable, wherein the computer readable medium comprises instructions that cause the control electronics to carry out the method according to any of claims 1-9.

A thirteenth aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to (i) initiate a blood fluid removal session with initial system parameters; (ii) acquire a first set of data regarding one or more patient physiological parameters; (iii) store the first data set in a most effective to date data set memory; (iv) associate the initial system parameters in an increased effectiveness lookup table with the first data set; (v) adjust at least one parameter of the blood fluid removal session to arrive at adjusted system parameters; (vi) acquire a second set of data regarding the one or more patient physiological parameters after the at least one parameter of the blood fluid removal session has been adjusted; and (vii) if at least one value of the second data set is closer to the target value than a corresponding at least one value of the first data set: replace the first data set in the most effective to date data set memory with the second data set; store in the increased effectiveness lookup table data regarding the second data set; and associate data regarding the adjusted system parameters with the second data set.

A fourteenth aspect is a computer-readable medium comprising instructions that, when executed by a blood fluid removal device, cause the device to (a) initiate a blood fluid removal session with initial system parameters; (b) acquire a first set of data regarding one or more patient physiological parameters; store the first data set in a most effective to date data set memory; (c) associate the initial system parameters in an increased effectiveness lookup table with the first data set; (d) adjust at least one parameter of the blood fluid removal session to arrive at adjusted system parameters; (e) acquire a second set of data regarding the one or more patient physiological parameters after the at least one parameter of the blood fluid removal session has been adjusted; and (f) if a at least one value of the second data set is closer to the target value than a corresponding at least one value of the first data set: replace the first data set in the most effective to date data set memory with the second data set; store in the increased effectiveness lookup table data regarding the second data set; and associate data regarding the adjusted system parameters with the second data set.

A fifteenth aspect is a method carried out by a blood fluid removal system, comprising: (a) acquiring data regarding one or more of: (i) one or more patient physiological parameters; and (ii) time since last blood fluid removal session; (b) acquiring data regarding one or more target outcomes of a blood fluid removal session; (c) determining whether at least one of the one or more target outcomes is within a predetermined range of a at least one corresponding prior target outcome stored in a lookup table, wherein the lookup table comprises data regarding system parameters used in one or more prior blood fluid removal sessions of the patient; (d) determining whether the at least one target outcome was achieved with the system parameters used in the prior blood fluid removal session; (e) if the at least one target outcome is determined to have been achieved, determining whether at least one of the patient parameters or time since last blood fluid removal session is within a predetermined range of at least one corresponding parameter stored in the lookup table; and (f) initiating a blood fluid removal session employing the system parameters used the prior blood fluid removal session if the at least one patient parameter or time since last blood fluid removal session is determined to be within a predetermined range.

A sixteenth aspect is a method of the fifteenth aspect, wherein the at least one of the one or more patient parameters are selected from the group consisting of blood pressure, heart rate, pH and concentration of an electrolyte.

A seventeenth aspect is a method of the sixteenth aspect, wherein the electrolyte is potassium.

An eighteenth aspect is a method of any of aspects 15-17, wherein the system parameters comprise one or more of fluid removal rate and concentration of one or more electrolyte.

A nineteenth aspects is a blood fluid removal system, comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a method according to any of aspects 15-18.

A twentieth aspect is a system of the nineteenth aspect, wherein the blood fluid removal medium and the control electronics are housed within a blood fluid removal device.

A twenty-first aspect is a system of aspect 19 or 20, further comprising a computer readable, wherein the computer readable medium comprises instructions that cause the control electronics to carry out the method according to any of aspects 15-18.

A twenty-second aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) acquire data regarding one or more of: one or more patient physiological parameters; and time since last blood fluid removal session; (ii) acquire data regarding one or more target outcomes of a blood fluid removal session; (iii) determine whether at least one of the one or more target outcomes is within a predetermined range of a at least one corresponding prior target outcome stored in a lookup table, wherein the lookup table comprises data regarding system parameters used in one or more prior blood fluid removal sessions of the patient; (iv) determine whether the at least one target outcome was achieved with the system parameters used in the prior blood fluid removal session; (v) if the at least one target outcome is determined to have been achieved, determine whether at least one of the patient parameters or time since last blood fluid removal session is within a predetermined range of at least one corresponding parameter stored in the lookup table; and (vi) initiate a blood fluid removal session employing the system parameters used the prior blood fluid removal session if the at least one patient parameter or time since last blood fluid removal session is determined to be within a predetermined range.

A twenty-third aspect is a computer-readable medium comprising instructions that, when executed by a blood fluid removal device, cause the device to (a) acquire data regarding one or more of: one or more patient physiological parameters; and time since last blood fluid removal session; (b) acquire data regarding one or more target outcomes of a blood fluid removal session; (c) determine whether at least one of the one or more target outcomes is within a predetermined range of a at least one corresponding prior target outcome stored in a lookup table, wherein the lookup table comprises data regarding system parameters used in one or more prior blood fluid removal sessions of the patient; (d) determine whether the at least one target outcome was achieved with the system parameters used in the prior blood fluid removal session; (e) if the at least one target outcome is determined to have been achieved, determine whether at least one of the patient parameters or time since last blood fluid removal session is within a predetermined range of at least one corresponding parameter stored in the lookup table; and (f) initiate a blood fluid removal session employing the system parameters used the prior blood fluid removal session if the at least one patient parameter or time since last blood fluid removal session is determined to be within a predetermined range.

A twenty-fourth aspect is a method carried out by a blood fluid removal system, comprising: (a) collecting first data regarding a patient, the data including one or more of a physiological parameter and time since last blood fluid removal session; (b) collecting second data regarding system parameters employed in blood fluid removal sessions of the patient; (c) determining, based on the first and second collected data, whether at least one physiological parameter of the patient improved as a result of the system parameters employed; (d) determining whether a value of current patient data is within a predetermined range of a corresponding value of first collected data; and (e) employing the system parameters that resulted in improvement, if such parameters are determined to exist and if the current patient data is determined to be within the predetermined range.

A twenty-fifth aspect is a blood fluid removal system, comprising: (a)_a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a method according to aspect 24.

A twenty-sixth aspect is a system of aspect 25, wherein the blood fluid removal medium and the control electronics are housed within a blood fluid removal device.

A twenty-seventh aspect is a system of aspect 25 or claim 24, further comprising a computer readable, wherein the computer readable medium comprises instructions that cause the control electronics to carry out the method according to aspect 24.

A twenty-eighth aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) collect first data regarding a patient, the data including one or more of a physiological parameter and time since last blood fluid removal session; (ii) collect second data regarding system parameters employed in blood fluid removal sessions of the patient; (iii) determine, based on the first and second collected data, whether at least one physiological parameter of the patient improved as a result of the system parameters employed; (iv) determine whether a value of current patient data is within a predetermined range of a corresponding value of first collected data; and (v) employ the system parameters that resulted in improvement, if such parameters are determined to exist and if the current patient data is determined to be within the predetermined range.

A twenty-ninth aspect is a computer-readable medium comprising instructions that, when executed by a blood fluid removal device, cause the device to (a) collect first data regarding a patient, the data including one or more of a physiological parameter and time since last blood fluid removal session; (b) collect second data regarding system parameters employed in blood fluid removal sessions of the patient; (c) determine, based on the first and second collected data, whether at least one physiological parameter of the patient improved as a result of the system parameters employed; (d) determine whether a value of current patient data is within a predetermined range of a corresponding value of first collected data; and (e) employ the system parameters that resulted in improvement, if such parameters are determined to exist and if the current patient data is determined to be within the predetermined range.

Thus, systems, devices and methods for ADAPTIVE SYSTEM FOR BLOOD FLUID REMOVAL are described. Those skilled in the art will recognize that the preferred embodiments described herein may be altered or amended without departing from the true spirit and scope of the disclosure, as defined in the accompanying claims.

In the claims that follow, the designators "first", "second", "third" and the like are used for purposes of distinguishing between elements and not for purposes of enumerating the elements or for defining a sequence of the elements. For example, a "third" data set does not necessarily imply that there are three data sets but rather that the "third" data set is distinct from the "first" data set. By way of further example, a "third" data set need not be obtained after a "first" data set.

What is claimed is:

1. A method carried out by a blood fluid removal system, comprising:
    initiating a blood fluid removal session, using a blood fluid removal device, with initial system parameters;
    acquiring a first set of data regarding one or more patient physiological parameters, wherein the one or more patient physiological parameters include at least one of pH and concentration of an electrolyte;
    storing the first data set in a most effective to date data set memory;
    associating the initial system parameters in an increased effectiveness lookup table with the first data set;
    adjusting at least one parameter of the blood fluid removal session by adjusting the blood fluid removal system to arrive at adjusted system parameters;
    acquiring a second set of data regarding the one or more patient physiological parameters after the at least one parameter of the blood fluid removal session has been adjusted; and
    determining which of the first and second set of data includes at least one value closer to a target value; storing in the increased effectiveness lookup table data regarding the data set having at least one value closer to the target value; and associating data regarding the adjusted system parameters with the data set having at least one value closer to the target value; and
    repeating the process beginning with acquiring a first set of data regarding one or more patient physiological parameters;
    storing the first data set in a least effective to date data set memory;
    associating the initial system parameters in a decreased effectiveness lookup table with the first data set prior to adjusting the at least one parameter of the blood fluid removal session;
    determining which of the first and second set of data includes at least one value further from the target value; storing in the decreased effectiveness lookup table data regarding the data set having at least one value further from the target value; and associating data regarding the adjusted system parameters with the data set having at least one value further from to the target value;
    replacing the data in the least effective to date data set with the data from the data set having at least one value further from the target value; and
    continuing the blood fluid removal session with the system parameters in the most effective to date data set;
    wherein the blood fluid removal system performs at least one blood fluid removal process selected from the group consisting of ultrafiltration, hemofiltration, hemodialysis, hemodiafiltration and peritoneal dialysis.

2. The method of claim 1, further comprising:
    further adjusting at least one parameter of the blood fluid removal session to arrive at further adjusted system parameters;
    acquiring a third set of data regarding the one or more patient physiological parameters after the at least one parameter of the blood fluid removal session has been further adjusted; and
    determining which of the first and third sets of data includes at least one value and storing in the increased effectiveness lookup table data regarding the data set and associating data regarding the further adjusted system parameters with the data set having at least one value closer to the target value.

3. The method of claim 1, further comprising:
    further adjusting at least one parameter of the blood fluid removal session to arrive at further adjusted system parameters;
    acquiring a fourth set of data regarding the one or more patient physiological parameters after the at least one parameter of the blood fluid removal session has been further adjusted; and
    determining which of the first, second and fourth set of data includes at least one value further from the target value; and storing in the decreased effectiveness lookup table data regarding the data set having at least one value further from the target value and associating data regarding the further adjusted system parameters with the data set having at least one value further from the target value.

4. The method of claim 1, further comprising:
    acquiring a fifth set of data regarding one or more patient physiological parameters;
    comparing the fifth data set to the increased effectiveness lookup table; and
    determining whether at least one parameter of the data set stored in the increased effectiveness table is within a predetermined range of the fifth data set; and adjusting the system parameters associated with the data set stored in the increased effectiveness lookup table if the at least one parameter of the data set stored in the increased effectiveness lookup table is within the predetermined range of the fifth data set.

5. The method of claim 1, further comprising:
    stopping the blood fluid removal session;
    acquiring a sixth set of data regarding one or more patient physiological parameters;
    comparing the sixth data set to the increased effectiveness lookup table; and
    initiating a second blood fluid removal session with the system parameters associated with the data set stored in the increased effectiveness lookup table if at least one parameter of a data set stored in the increased effectiveness lookup table is within a predetermined range of at least one parameter of the sixth data set.

6. The method of claim 1, wherein the at least one of the one or more patient parameters also include at least one parameter selected from the group consisting of blood pressure and heart rate.

7. The method of claim 1, wherein the electrolyte is potassium.

8. The method of claim 1, wherein the system parameters comprise one or more of fluid removal rate and concentration of one or more electrolyte.

9. A non-transitory computer-readable medium comprising instructions that, when executed by a blood fluid removal device, cause the device to
    initiate a blood fluid removal session with initial system parameters;
    acquire a first set of data regarding one or more patient physiological parameters, wherein the one or more patient physiological parameters include at least one of pH and concentration of an electrolyte;

store the first data set in a most effective to date data set memory;

associate the initial system parameters in an increased effectiveness lookup table with the first data set;

adjust at least one parameter of the blood fluid removal session by adjusting the blood fluid removal system to arrive at adjusted system parameters;

acquire a second set of data regarding the one or more patient physiological parameters after the at least one parameter of the blood fluid removal session has been adjusted; and determine which of the first and second set of data includes at least one value closer to a target value; store in the increased effectiveness lookup table data regarding the data set having at least one value closer to the target value; and associate data regarding the adjusted system parameters with the data set having at least one value closer to the target value;

repeat the process beginning with acquiring a first set of data regarding one or more patient physiological parameters;

store the first data set in a least effective to date data set memory;

associate the initial system parameters in a decreased effectiveness lookup table with the first data set prior to adjusting the at least one parameter of the blood fluid removal session;

determine which of the first and second set of data includes at least one value further from the target value; store in the decreased effectiveness lookup table data regarding the data set having at least one value further from the target value; and associate data regarding the adjusted system parameters with the data set having at least one value further from to the target value;

replace the data in the least effective to date data set with the data from the data set having at least one value further from the target value; and continue the blood fluid removal session with the system parameters in the most effective to date data set;

wherein the blood fluid removal system performs at least one blood fluid removal process selected from the group consisting of ultrafiltration, hemofiltration, hemodialysis, hemodiafiltration and peritoneal dialysis.

* * * * *